United States Patent [19]
Maeda et al.

[11] Patent Number: 5,880,274
[45] Date of Patent: Mar. 9, 1999

[54] CAT-MOUSE HETEROHYBRIDOMA AND GENE FRAGMENT CODING FOR CONSTANT REGION OF FELINE IMMUNOGLOBULIN

[75] Inventors: Hiroaki Maeda; Yasuyuki Eda; Kazuhiko Kimachi; Yoichi Ono; Sachio Tokiyoshi, all of Kumamoto, Japan

[73] Assignee: Juridical Foundation, The Chemo-Sero-Therapeutic Research Institute, Kumamoto, Japan

[21] Appl. No.: 559,947

[22] Filed: Nov. 17, 1995

Related U.S. Application Data

[62] Division of Ser. No. 247,486, May 23, 1994, Pat. No. 5,504,198, which is a continuation of Ser. No. 565,233, Aug. 10, 1990, abandoned.

[30] Foreign Application Priority Data

| Aug. 10, 1989 | [JP] | Japan | 1-208822 |
| Sep. 30, 1989 | [JP] | Japan | 1-255424 |
| Dec. 28, 1989 | [JP] | Japan | 1-344465 |

[51] Int. Cl.$^6$ .......................... C07H 21/04; C12N 15/00; C12N 5/00
[52] U.S. Cl. ................... 536/23.53; 435/172.3; 435/172.2; 435/240.2
[58] Field of Search .............. 536/23.53; 435/172.3, 435/172.2

[56] References Cited

U.S. PATENT DOCUMENTS 4,816,567  3/1989  Cabilly et al. ........................ 530/387

FOREIGN PATENT DOCUMENTS 8 702 671  10/1986  WIPO .

OTHER PUBLICATIONS

Science, V. 229, Sep. 20, 1985, S.L. Morrison, "Transfectomas Provide Novel Chimeric Antibodies", pp. 1202–1207.
Trends in Biotechnology, vol. 6, No. 2, Feb. 1988, G. Williams, "Novel Antibody Reagents: Production and Potential", pp. 36–39, 42.
Proceedings of the National Academy of Science of the USA, Oct. 1989, vol. 86, No. 19, Schneiderman et al., Expressioon of 12 rabbit IgA C genes as Chemeric rabbit-–mouse IgA antibodies.
Capra et al., Antibody Structure and Molecular Immunology, vol. 36, No. 3, 1975.
Capra et al., Federatin of European Biochemical Societies, Ninth Meeting, vol. 36: 3–18, 1974.
Capra et al., Chemical Abstracts 84; 1976, p. 424, 84:103 680K.

*Primary Examiner*—Suzanne E. Ziska
*Attorney, Agent, or Firm*—Foley & Lardner

[57] ABSTRACT

A Gene fragment which comprises a DNA sequence coding for an amino acid sequence of a constant region of feline immunoglobulin λ chain; a gene fragment which comprises a DNA sequence coding for an amino acid sequence of a constant region of feline immunoglobulin κ chain; a gene fragment which comprises a DNA sequence coding for the constant region of feline immunoglobulin γ chain; a recombinant DNA molecule coding for an amino acid sequence of a mouse-cat chimeric antibody which comprises a gene fragment coding for an amino acid sequence of a variable region of a mouse immunoglobulin and a gene fragment coding for an amino acid sequence of a constant region of a feline immunoglobulin wherein the latter gene fragment is linked to the 3' site of the former gene fragment; a polypeptide of a mouse-cat chimeric antibody which is expressed from a cell transformed with an expression vector for cells wherein said recombinant DNA molecule coding for an amino acid sequence of the mouse-cat chimeric antibody is incorporated; a cat-mouse heterohybridoma which produces feline immunoglobulin; and a process for preparing a feline immunoglobulin gene.

33 Claims, 17 Drawing Sheets

FIG. 6

```
CAGCCCAAGT CGGCCCCCTC GGTCACACTC TTCCCACCCT CCAGTGAGGA GCTCAGCGCA
AACAAGGCCA CCCTGGTGTG TCTCGTCAGT GACTTCTACC CCAGCGGCTT GACGGTGGCC
TGGAAGGAAG ATGGCACCCC CATCACCAAG CATCACCAAG CCACCAAGCC CTCCAGACAG
AGCAACAACA AGTACGCGGC CAGCAGCTAC CTGAGCCTGT CACCGAACGA GTGGAAATCT
CACAGCAGAT ACACCTGCCA GGTCACGCAC GAGGGGAGCA CTGTGGAGAA GAGTGTGGTC
CCTGCAGAGT GCCCCTTAG
```

FIG. 7

GlnProLysSerAlaProSerValThrLeuPheProProSerSerGluGluLeuSerAla
AsnLysAlaThrLeuValCysLeuValSerAspPheTyrProSerGlyLeuThrValAla
TrpLysGluAspGlyThrProIleThrLysGlyValGluThrThrLysProSerArgGln
SerAsnAsnLysTyrAlaAlaSerSerTyrLeuSerLeuSerProAsnGluTrpLysSer
HisSerArgTyrThrCysGlnValThrHisGluGlySerThrValGluLysSerValVal
ProAlaGluCysPro

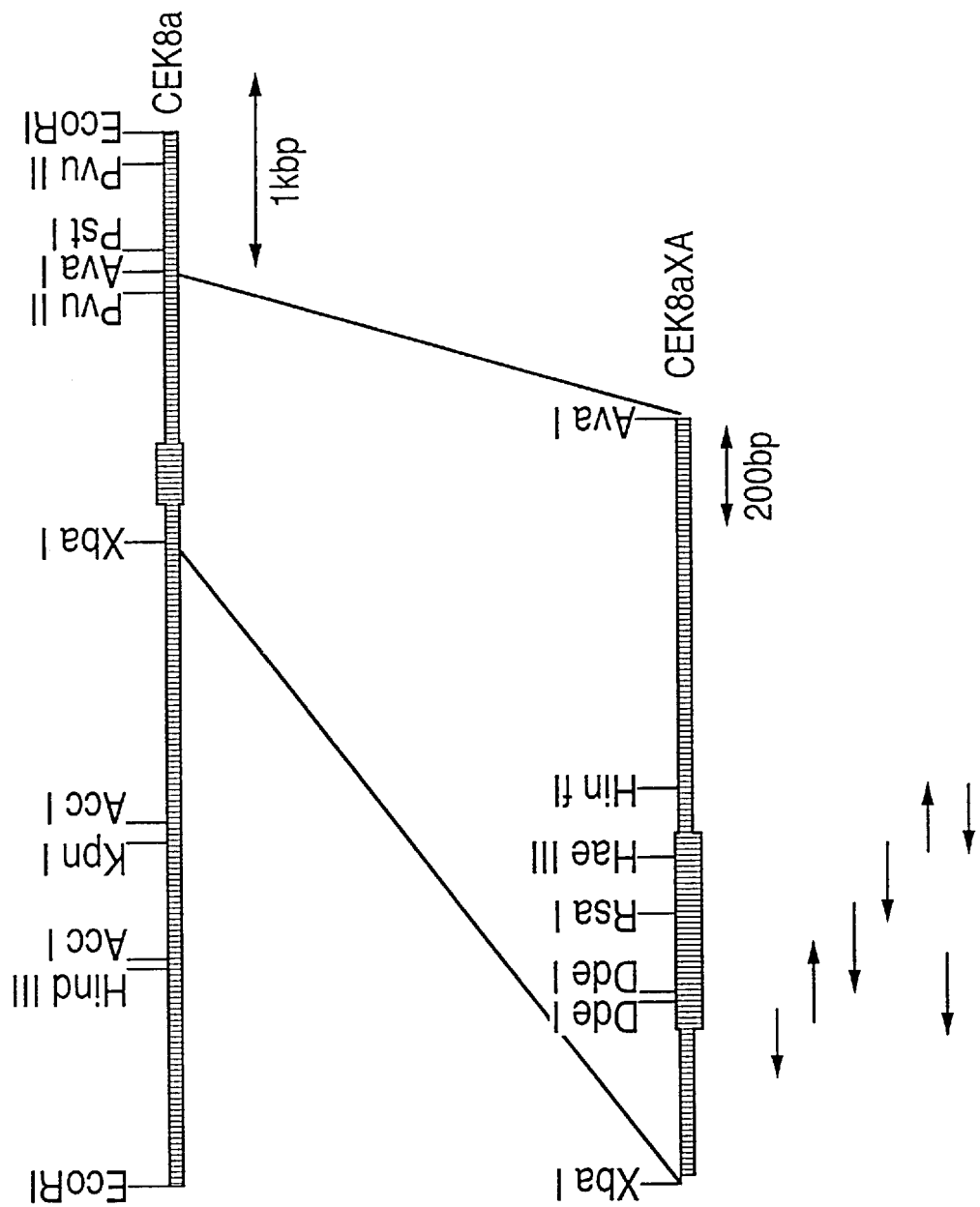

FIG. 11

```
AGTGATGCTC AGCCATCTGT CTTTCTCTTC CAACCATCTC TGGACGAGTT ACATACAGGA
AGTGCCTCTA TCGTGTGCAT ATTGAATGAC TTCTACCCCA AAGAGGTCAA TGTCAAGTGG
AAAGTGGATG GCGTAGTCCA AACAAAGGCA TCCAAGGAGA GCACCACAGA GCAGAACAGC
AAGGACAGCA CCTACAGCCT CAGCAGCACC CTGACGATGT CCAGGACGGA GTACCAAAGT
CATGAAAAGT TCTCCTGCGA GGTCACTCAC AAGAGCCTGG CCTCCACCCT CGTCAAGAGC
TTCAACAGGA GCGAGTGTCA GAGAGAGTAG
```

FIG. 12

SerAspAlaGlnProSerValPheLeuPheGlnProSerLeuAspGluLeuHisThrGly
SerAlaSerIleValCysIleLeuAsnAspPheTyrProLysGluValAsnValLysTrp
LysValAspGlyValValGlnThrLysAlaSerLysGluSerThrThrGluGlnAsnSer
LysAspSerThrTyrSerLeuSerSerThrLeuThrMetSerArgThrGluTyrGlnSer
HisGluLysPheSerCysGluValThrHisHisLysSerLeuAlaSerThrLeuValLysSer
PheAsnArgSerGluCysGlnArgGlu

Fig. 17

```
CCACCACGGC CCCATCGGTG TTCCCACTGG CCCCCAGCTG CGGGACCACA
TCTGGCGCCA CCGTGGCCCT GGCCTGCCTG GTGTTAGGCT ACTTCCCTGA
GCCGGTGACC GTGTCCTGGA ACTCCGGCGC CCTGACCAGC GGTGTGCACA
CCTTCCCGGC CGTCCTGCAG GCCTCGGGGC TGTACTCTCT CAGCAGCATG
GTGACAGTGC CCTCCAGCAG GTGGCTCAGT GACACCTTCA CCTGCAACGT
GGCCCACCCG CCCAGCAACA CCAAGGTGGA CAAGACCGTG CGCAAAACAG
ACCACCCACC GGGACCCAAA CCCTGCGACT GTCCCAAATG CCCACCCCCT
GAGATGCTTG GAGGACCGTC CATCTTCATC TTCCCCCCAA AACCCAAGGA
CACCCTCTCG ATTTCCCGGA CGCCCGAGGT CACATGCTTG GTGGTGGACT
TGGGCCCAGA TGACTCCGAT GTCCAGATCA CATGGTTTGT GGATAACACC
CAGGTGTACA CAGCCAAGAC GAGTCCGCGT GAGGAGCAGT TCAACAGCAC
CTACCGTGTG GTCAGTGTCC TCCCCATCCT ACACCAGGAC TGGCTCAAGG
GGAAGGAGTT CAAGTGCAAG GTCAACAGCA AATCCCTCCC CTCCCCCATC
GAGAGGACCA TCTCCAAGGC CAAAGGACAG CCCCACGAGC CCCAGGTGTA
CGTCCTGCCT CCAGCCCAGG AGGAGCTCAG CAGGAACAAA GTCAGTGTGA
CCTGCCTGAT CAAAAGCTTC CACCCGCCTG ACATTGCCGT CGAGTGGGAG
ATCACCGGAC AGCCGGAGCC AGAGAACAAC TACCGGACGA CCCCGCCCCA
GCTGGACAGC GACGGGACCT ACTTCGTGTA CAGCAAGCTC TCGGTGGACA
GGTCCCACTG GCAGAGGGGA AACACCTACA CCTGCTCGGT GTCACACGAA
GCTCTGCACA GCCACCACAC ACAGAAATCC CTCACCCAGT CTCCGGGTAA
ATGA
```

FIG. 18

```
Thr Thr Ala Pro Ser Val Phe Pro Leu Ala Pro Ser Cys Gly
                                            (A)
Thr Thr Ser Gly Ala Thr Val Ala Leu Ala Cys Leu Val Leu
Gly Tyr Phe Pro Glu Pro Val Thr Val Ser Trp Asn Ser Gly
Ala Leu Thr Ser Gly Val His Thr Phe Pro Ala Val Leu Gln
Ala Ser Gly Leu Tyr Ser Leu Ser Ser Met Val Thr Val Pro
Ser Ser Arg Trp Leu Ser Asp Thr Phe Thr Cys Asn Val Ala
        (B)
His Pro Pro Ser Asn Thr Lys Val Asp Lys Thr Val Arg Lys
Thr Asp His Pro Pro Gly Pro Lys Pro Cys Asp Cys Pro Lys
Cys Pro Pro Pro Glu Met Leu Gly Gly Pro Ser Ile Phe Ile
Phe Pro Pro Lys Pro Lys Asp Thr Leu Ser Ile Ser Arg Thr
Pro Glu Val Thr Cys Leu Val Val Asp Leu Gly Pro Asp Asp
Ser Asp Val Gln Ile Thr Trp Phe Val Asp Asn Thr Gln Val
Tyr Thr Ala Lys Thr Ser Pro Arg Glu Glu Gln Phe Asn Ser
            (C)
Thr Tyr Arg Val Val Ser Val Leu Pro Ile Leu His Gln Asp
Trp Leu Lys Gly Lys Glu Phe Lys Cys Lys Val Asn Ser Lys
Ser Leu Pro Ser Pro Ile Glu Arg Thr Ile Ser Lys Ala Lys
Gly Gln Pro His Glu Pro Gln Val Tyr Val Leu Pro Pro Ala
Gln Glu Glu Leu Ser Arg Asn Lys Val Ser Val Thr Cys Leu
                    (D)
Ile Lys Ser Phe His Pro Pro Asp Ile Ala Val Glu Trp Glu
Ile Thr Gly Gln Pro Glu Pro Glu Asn Asn Tyr Arg Thr Thr
Pro Pro Gln Leu Asp Ser Asp Gly Thr Tyr Phe Val Tyr Ser
Lys Leu Ser Val Asp Arg Ser His Trp Gln Arg Gly Asn Thr
Tyr Thr Cys Ser Val Ser His Glu Ala Leu His Ser His His
Thr Gln Lys Ser Leu Thr Gln Ser Pro Gly Lys
```

FIG. 20

GGTGGCTCTAGTCATGCATTCCCCTGCTGATTTGCATGTTACCAGAGCACAGCCCACATC

TAAGATTTCTTCAGCTGGTGTTTAGGACAATGGCAGAAAGTCACTCTCAGTGAGGATACA

CCATCAGCATGAGGGTCCTTGCTGAGCTCCTGGGGCTGCTGCTGTTCTGCTTTTTAGGCA
        MetArgValLeuAlaGluLeuLeuGlyLeuLeuLeuPheCysPheLeu
        LEADER

GTGAACAGAGTGAAACGTATGTAATGCTGTCTGATTTGTGATGTATCTACAATTGTTCAC

ATGGTATTGTGTATGTTTCCCACCTCAGGTGTGAGATGTGACATCCAGATGAACCAGTCT
                                    GlyValArgCysAspIleGlnMetAsnGlnSer
                                          FR1

CCATCCAGTCTGTCTGCATCCCTTGGAGACACAATTACCATCACTTGCCATGCCAGTCAG
ProSerSerLeuSerAlaSerLeuGlyAspThrIleThrIleThrCysHisAlaSerGln
                                                            CDR1

AACATTAATGTTTGGTTAAGCTGGTACCAGCAGAAACCAGGAAATATTCCTAAACTATTG
AsnIleAsnValTrpLeuSerTrpTyrGlnGlnLysProGlyAsnIleProLysLeuLeu
                                    FR2

ATCTATAAGGCTTCCAAATTGCACACAGGCGTCCCATCAAGGTTTAGTGGCAGTGGATCT
IleTyrLysAlaSerLysLeuHisThrGlyValProSerArgPheSerGlySerGlySer
      CDR2                     FR3

GGAACAGGTTTCACATTAACCATCAGCAGCCTGCAGCCTGAAGACATTGCCACTTACTAC
GlyThrGlyPheThrLeuThrIleSerSerLeuGlnProGluAspIleAlaThrTyrTyr

TGTCAACACGGTCAAAGTTATCCGTACAGCTTCGGAGGGGGGACCAAGCTGGAAATAAAA
CysGlnHisGlyGlnSerTyrProTyrSerPheGlyGlyGlyThrLysLeuGluIleLys
    CDR3              Jk2

CGTAAGTAGTCTTCTCAA

CAT-MOUSE HETEROHYBRIDOMA AND GENE FRAGMENT CODING FOR CONSTANT REGION OF FELINE IMMUNOGLOBULIN

This application is a division of application Ser. No. 08/247,486, filed May 23, 1994 now U.S. Pat. No. 5,504,198 which is a continuation of application Ser. No. 07/565,233 filed Aug. 10, 1990, now abandoned.

The present invention relates to a novel feline monoclonal antibody which is expected to be useful for diagnosis, treatment and prevention of feline diseases, especially feline infectious diseases. More particularly, it relates to a novel cat-mouse heterohybridoma capable of producing a feline immunoglobulin, a gene fragment coding for a constant region of feline immunoglobulin and a feline chimeric antibody produced by utilizing said gene fragment.

TECHNICAL BACKGROUND AND PRIOR ART

From ancient times, cats have been favorably treated as a pet by humans. In modern Europe and America, they are called "Companion species" and now becoming a member of human society. On the other hand, cats have hitherto been used as an experimental animal in various fields including medicine, pharmacy, animal husbandry, veterinary, psychology etc. They are also used as a minimal disease cat in recent years in tests for determination of effect and safety of drugs, and hence, usefulness thereof for humans becoming greater and greater. In any case, it is earnestly desired to establish a method for more certain diagnosis, treatment and prevention of feline diseases, especially feline infectious diseases in order to keep cats in healthy conditions thereof.

There are many feline viral diseases, and among them, those caused by feline rhinotracheitis virus, feline parvovirus, feline infectious peritonitis, etc. are acute diseases having a very high lethality rate. Although vaccines for prevention of these diseases have been developed, only symptomatic therapy such as by antibiotics and sulfonamides which prevents secondary bacterial infections has been available for treating those cats infected and attacked with these diseases, and hence, the conventional methods for treating these diseases are still insufficient.

Hitherto, a hyperimmune serum and an immunoglobulin derived from serum have been utilized for treatment of these diseases and confirmed to be effective. However, with the popularity of the idea for kindly treatment of animals, feline serum materials have become hard to obtain, and hence, this treatment can not be used nowadays. Therefore, development of a monoclonal antibody capable of neutralizing the infected viruses in place of the conventional hyperimmune serum will greatly contribute to the treatment of these viral diseases.

As mentioned above, a monoclonal antibody having a neutralizing activity against viruses can be used as the alternative to the hyperimmune serum. Hitherto, basic techniques of preparing monoclonal antibodies have been established mainly for a mouse monoclonal antibody. Monoclonal antibodies produced by cells such as hybridomas can advantageously be obtained in a large amount and semipermanently and solve the problem of material insufficiency. However, the monoclonal antibody in this case should be a feline monoclonal antibody instead of the conventional mouse monoclonal antibody in order to eliminate side effects such as anaphylatic shock, serum disease, etc. caused by the use in cats of the mouse monoclonal antibody which acts as a heteroprotein to cats.

Methods for preparing such feline monoclonal antibody as a drug for treating the feline viral diseases include:

(1) a method using a cat-cat hybridoma;

(2) a method using a feline lymphocyte transformed with some viral or chemical agent;

(3) a method using a cat-mouse heterohybridoma;

(4) a method using a cat-(cat-mouse) hybridoma derived from a cat-mouse heterohybridoma; and (5) a method by gene recombination techniques of a mouse (V)—cat (C) chimeric monoclonal antibody wherein a variable (V) region which binds to an antigen is derived from a mouse monoclonal antibody having neutralizing activity against viruses and a constant (C) region which is responsible for antigenicity, immunogenicity and physiological activity is derived from a feline monoclonal antibody.

However, none of the above methods have hitherto been reported to be effectively used.

In the method (1), a fusion efficiency is quite low and no appropriate myeloma strain is available. In case of the method (2), there are no appropriate virus corresponding to EB virus in case of human and no appropriate chemical agents. The methods (3) and (4) will have much difficulty (for example, a stability problem etc.) in obtaining the desired feline monoclonal antibody with high efficiency in view of the case of preparation of a human monoclonal antibody. Therefore, it is expected that the method (5) using the chimeric monoclonal antibody is the most realizable method among these five methods.

The chimeric monoclonal antibody is prepared by incorporating a plasmid vector containing a mouse (V)—cat (C) chimeric antibody gene into an animal host cell (e.g. mouse myeloma cell), expressing said gene in the host cell and collecting the monoclonal antibody from a supernatant of the culture, wherein said mouse (V)—cat (C) chimeric antibody gene is such that a V (variable) gene is cloned from a mouse-mouse hybridoma capable of producing a mouse monoclonal antibody as a source of a gene coding for a V region, a C (constant) gene is cloned from a feline cell such as a feline antibody-producing cell capable of producing a feline monoclonal antibody as a source of a gene coding for a C region and said V gene and said C gene are linked to each other. Several reports are found as to human chimeric antibodies (Japanese Patent First Publications Nos. 155132/1985 and 47500/1986).

As mentioned above, a gene coding for an amino acid sequence in a variable (V) region of an antibody molecule capable of binding to a desired antigen and a gene coding for an amino acid sequence in a constant (C) region of a feline immunoglobulin are required for preparing the feline chimeric antibody. The gene coding for the variable (V) region of the chimeric antibody is derived from a cell capable of producing a mouse monoclonal antibody having a neutralizing activity against the above mentioned various feline viruses and said cell can be prepared rather easily by the conventional mouse-mouse hybridoma producing procedure. However, the gene coding for the constant (C) region of the chimeric antibody, i.e. the gene coding for the constant (C) region of the feline immunoglobulin is still unknown in its structure and has never been cloned. Therefore, in order to prepare the feline chimeric antibody, it is inevitably required to find the gene coding for the amino acid sequence of the constant (C) region of the feline immunoglobulin.

In addition, although there is much difficulty in obtaining the monoclonal antibody showing a desired specificity in case of the methods (1) to (4), materials (cell strains) effective for preparing the chimeric antibody can effectively be provided in case of the method (5) since any cell which produces the feline immunoglobulin regardless of its specificity can preferably be employed as material for providing a gene coding for the C region of the feline immunoglobulin for preparing the chimeric antibody.

BRIEF SUMMARY OF THE INVENTION

Under the circumstances, the present inventors have succeeded in preparing cat-mouse hybridomas which produce the feline immunoglobulin, in isolating a gene coding for the amino acid sequence in the constant (C) region of the feline immunoglobulin using said hybridoma cells and feline cells, and in preparing a feline chimeric antibody using the gene fragment coding for the constant (C) region of the feline immunoglobulin.

An object of the invention is to provide a hitherto unreported cat-mouse heterohybridoma capable of producing the feline immunoglobulin and a hitherto genetically unanalyzed DNA fragment coding for an amino acid sequence in the constant (C) region of the feline immunoglobulin. Another object of the invention is to provide a process for preparing the feline chimeric antibody using said DNA fragment coding for the amino acid sequence in the constant (C) region of the feline immunoglobulin, said chimeric antibody being useful in agents for diagnosis, treatment and prevention of feline diseases, especially infectious feline diseases, without showing side effects. These and other objects and advantages of the invention will be apparent to those skilled in the art from the following description.

BRIEF DESCRIPTION OF THE DRAWINGS

FIG. 6 shows a nucleotide sequence coding for the constant region of feline immunoglobulin λ chain present in the DNA fragment (T1-62) cloned by the present invention;

FIG. 7 shows a whole amino acid sequence of the constant region of feline immunoglobulin λ chain coded in the DNA fragment (T1-62) cloned by the present invention;

FIG. 10 shows a restriction enzyme map of a DNA fragment (CEκ8a) coding for the constant region of feline immunoglobulin κ chain cloned by the present invention and the regions (→) in which a nucleotide sequence was analyzed;

FIG. 11 shows a nucleotide sequence coding for the constant region of feline immunoglobulin κ chain present in the DNA fragment CEκ8a cloned by the present invention;

FIG. 12 shows a whole amino acid sequence of the constant region of feline immunoglobulin κ chain coded in the DNA fragment CEκ8a cloned by the present invention;

FIG. 17 shows a nucleotide sequence coding for the constant region of feline immunoglobulin γ chain present in a cDNA fragment T1CB1a cloned by the present invention;

FIG. 18 shows a whole amino acid sequence of the constant region of feline immunoglobulin γ chain coded in a cDNA fragment T1CB1a cloned by the present invention;

FIG. 20 shows nucleotide and amino acid sequences of a Vκ region gene JP2gL411 isolated from anti-CPV mouse monoclonal antibody-producin cells.

DETAILED DESCRIPTION OF THE INVENTION

Figure 1B:
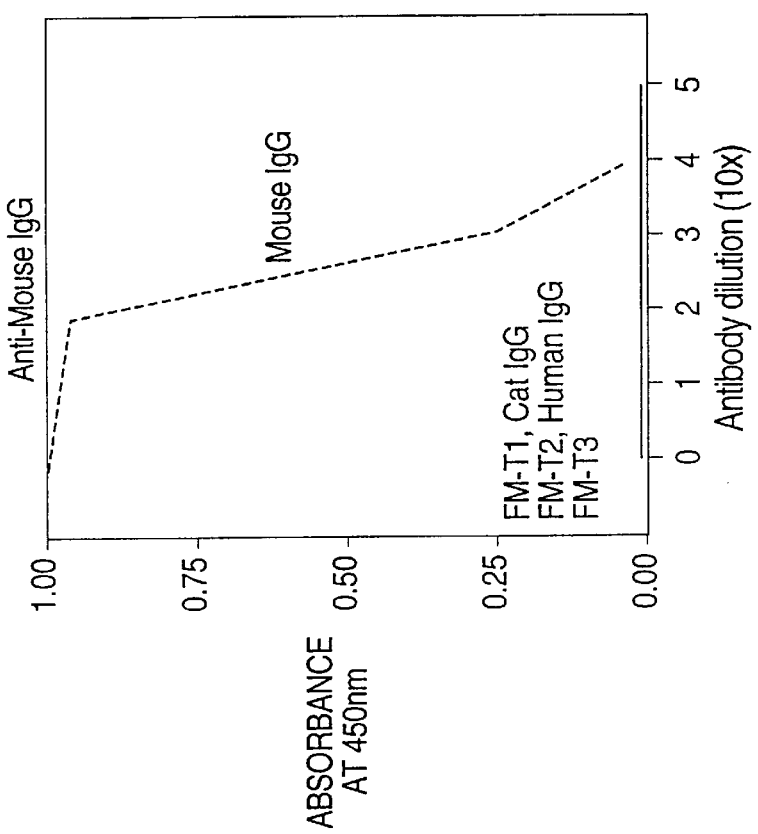
FIG. 1 shows the results of EIA using an anti-feline antibody proving that IgG produced by the cat-mouse hybridomas prepared by the present invention is a feline monoclonal antibody.

There are two approaches for isolating the gene coding for the amino acid sequence in the constant (C) region of the feline immunoglobulin. That is, the first is to construct a library from a chromosomal DNA in feline cells and then to clone the gene coding for the amino acid sequence in C region according to the conventional procedure [for example, see T. Maniatis "Molecular Cloning" Cold Spring Harbor Lab. (1982)], and the second is to construct a library by synthesizing cDNA from a messenger RNA (MRNA) of feline cells and then to clone the C region gene according to the conventional procedure [for example, see "DNA cloning Vol. I" ed. by D. M. Glover, IRL press (1985)].

For the screening procedure, there can be used mainly four processes; i.e. (1) a process which comprises purifying the antibody protein produced by the feline antibody-producing cell, analyzing the amino acid sequence of said protein, and synthesizing a nucleotide sequence corresponding to said amino acid sequence, and then using said nucleotide sequence as a probe for screening (hybridization); (2) a process by cross-hybridization using a probe synthesized by referring to a gene fragment of mouse and human immunoglobulin genes or nucleotide sequences thereof previously reported [for example, Sakano et al., Nature, 286, p676 (1980); E. E. Max et al., J. Biol. Chem., 256, p5116 (1981); J. W. Ellison et al., Nuc. Acids. Res., 10, p4071 (1982); and P. A. Heiter et al., Cell, 22, p197 (1980)]; (3) a process which comprises synthesizing a primer based on a nucleotide sequence on the analogy of an amino acid sequence of a feline antibody protein or a nucleotide sequence on the analogy of the mouse and human immunoglobulin genes previously reported and then screening based on the primer using the PCR procedure [R. Orlandi et al., Proc. Natl. Acad. Sci. USA, 86, p3833 (1989)]; and (4) a process which comprises expressing the feline antibody gene incorporated into an expression vector (e.g. λgt11) in E. coli or in an animal cell and screening the expression product by using an antiserum (or a monoclonal antibody) directed to the feline antibody protein. In case of the cDNA cloning procedure, all the above processes (1) to (4) can be used and in case of the chromosomal DNA cloning procedure the processes (1) to (3) can be used.

In any case, the screening process (1) using the feline antibody protein-producing cells is preferable in view of the cloning efficiency and is essential in case of the above second process for isolating the gene using the cDNA synthesized from messenger RNA. Although it is possible to use polyclonal cells such as spleen cells or lymph node cells as the antibody-producing cells, monoclonal cells are preferable in view of easiness of genetic analysis.

There are several methods for establishing the monoclonal antibody-producing cells as cited above (1) to (5). However, the methods (1) and (2) are extremely difficult to practice and the method (4) requires the cat-mouse heterohybridomas of the method (3). In conclusion, it is most important to obtain the cat-mouse heterohybridomas of the method (3).

The cat-mouse heterohybridomas can be prepared by the several methods previously disclosed. According to these methods, the present inventors have established cat-mouse heterohybridomas FM-T-1, -T2 and -T3 which produce the feline monoclonal antibody. Among these cat-mouse heterohybridomas, FM-T1 is the most preferable cell for preparing the gene of the present invention and has been deposited at the Fermentation Research Institute Agency of Industrial Science and Technology, Japan under Budapest Treaty under the accession number FERM BP-2947.

As mentioned above, the present inventors have cloned several kinds of gene fragments coding for the constant region of immunoglobulin from feline cells. The cloned gene fragments coding for the C region of feline immunoglobulin of the present invention were analyzed by comparing an amino acid sequence deduced from the nucleotide sequence thereof with the corresponding sequences of the C region genes of immunoglobulin from other animal species, and as a result, it has been found that each gene fragment of the present invention contains gene fragments coding for λ chain, κ chain and γ chain, respectively.

λ Chain of immunoglobulin has already been found in human [P. A. Hieter et al., Nature, 294, p536 (1981); G. F. Hollis et al., Nature 296, p321 (1982)] and in mouse [B. Blomberg et al., Proc. Natl. Acad. Sci. USA, 79, p530 (1982); J. Miller et al., Nature, 295, p428 (1982)] and has also been reported for other animal species such as rabbit [Duvoisin, MR. M. et al., J. Immunol., 136, p4297–4302 (1986)]. However, there has never been reported the feline λ chain of the present invention, the amino acid sequence thereof and the nucleotide sequence coding therefore.

The cDNA fragment coding for the constant region of feline immunoglobulin λ chain prepared as mentioned above has been analyzed for its nucleotide sequence. Then, the amino acid sequence of said constant region has been deduced from the nucleotide sequence and compared with the amino acid sequneces of the constant region of immunoglobulin λ chain derived from human, mouse, rabbit, etc. previously reported. As a result, it has been found that the constant region of feline immunoglobulin λ chain has a specific amino acid sequence at the N-terminal region of the polypeptide of said λ chain constant region which has the following amino acid sequence (A) at the N-terminal region of the first cysteine counted from the N-terminus of said polypeptide:

-Ser-Ala-xxx-xxx-xxx-xxx-xxx-xxx-Cys- (A)

wherein xxx means an optional amino acid residue.

From comparison among the amino acid sequence of the constant region of feline immunoglobulin λ chain analyzed in accordance with the present invention, the amino acid sequence of the constant region of canine immunoglobulin λ chain separately analyzed by the present inventors and various amino acid sequences of the constant region of immunoglobulin λ chain derived from several animal species, it has been found that the region -Ser-Ala- present at the N-terminus of the above cysteine is a region whose amino acid sequence varies with animal species such as cat, mouse, human, etc. In addition, it has been found that this region is quite well preserved among subclasses, for example, as an amino acid sequence of the constant region of human λ chain, and the above sequence (A) is supposed to be specific for the constant region of feline immunoglobulin λ chain. The region cloned by the present invention has the following amino acid sequence (A') which is one example of the preferable specific amino acid sequences present in the constant region of feline immunoglobulin λ chain.

-Ser-Ala-Asn-Lys-Ala-Thr-Leu-Val-Cys- (A')

The cat-mouse heterohybridoma of the present invention produces feline immunoglobulin containing a peptide of a λ chain C region having the above amino acid sequence (A) or (A'). The gene fragment coding for the constant region of feline immunoglobulin λ chain of the present invention also contains a DNA fragment coding for the above amino acid sequnece (A) or (A'). Such amino acid sequence contained in the above λ chain is believed to be an important amino acid sequence for determining the C region of the feline immunoglobulin λ chain and is firstly disclosed by the present invention. In the constant region polypeptide of the feline λ chain, the 11th - 9th amino acid sequence at the N-terminal region of from the second cysteine residue counted from the C-terminus is deemed to be the region whose amino acid sequence varies with species such as cat, dog, etc. as mentioned above, and it is found that the constant region of the feline immunoglobulin λ chain of the present invention has the corresponding specific sequence of -Pro-Asn-Glu-. One preferable example of the gene coding for the constant region of feline immunoglobulin λ chain is a gene fragment coding for the amino acid sequnece as shown in FIG. 7 and one example of the nucleotide sequence of said gene is as shown in FIG. 6.

On the analogy of the case of human and mouse [P. A. Hieter et al., Nature, 294, p536 (1981); G. F. Hollis et al., Nature, 296, p321 (1982); B. Blomberg et al., Proc. Natl. Acad. Sci. USA, 79, p530 (1982); J. Miller et al., Nature, 295, p428 (1982)], there is expected an existence of several subclasses in feline λ chain. In fact, Southern hybridization using the λ chain gene of the present invention and a feline chromosomal DNA shows an existence of C region genes of several subclasses belonging to the same feline λ chain gene in addition to the λ chain of the present invention. That is, there exist genes of different subclasses having a quite similar sequence to that of the gene fragment coding for the constant region of the feline immunoglobulin λ chain of the present invention. The feline λ chain gene of the present invention is believed to have sequences which cover also such gene fragments coding for amino acid sequneces of different subclasses. Therefore, such gene fragments coding for different subclasses can also be used as the feline λ chain gene as far as they have substantially the same sequence as that of the gene of the present invention. Cloning of such C genes of different subclasses can be carried out by using a part of the nucleotide sequence disclosed in the present invention as a probe. Alternatively, a chromosomal gene coding for the feline λ chain can also be cloned from feline cells using the feline immunoglobulin λ chain of the present invention as a probe.

κ Chain of immunoglobulin has also already been found in human and mouse [P. A. Hieter et al., Cell, 22, p197 (1980); H. Sakano et al., Nature 280, p288–294 (1979)] and also reported for other animal species such as rabbit [L. Emorine et al., Proc. Natl. Acad. Sci. USA, 80, p5709–5713 (1983)]. However, there has never been reported for the feline κ chain of the present invention, an amino acid sequence thereof and a nucleotide sequence coding therefor.

The present inventors have obtained a chromosomal DNA fragment which will code for the constant region of feline immunoglobulin κ chain by the above-mentioned procedure. The present inventors have also analyzed the nucleotide sequence of the chromosomal DNA fragment and have determined an amino acid sequence of the constant region. As a result of comparison of the amino acid sequence with those of the constant region of immunoglobulin κ chain derived from human, mouse, rabbit, etc., it has been found that the gene fragment of the present invention is a gene fragment coding for the constant region of immunoglobulin κ chain.

The gene fragment coding for the constant region of feline immunoglobulin κ chain of the present invention is a DNA sequence coding for a peptide comprising 109 amino acids and characterized in that four amino acids at the C-terminus thereof is -Cys-Gln-Arg-Glu. It is known that the C-terminus of the amino acid sequence of human or mouse κ chain constant region is Cys (cysteine) residue as previously reported. It is very rare that the amino acid sequence of the constant region contains additional three amino acids subsequent to the Cys residue present at the C-terminus like in the gene of the present invention coding for the constant region of feline immunoglobulin κ chain, which is characteristic for the constant region of feline immunoglobulin κ chain of the present invention. The gene coding for the constant region of feline immunoglobulin κ chain of the present invention contains the gene fragment as shown by the restriction enzyme map of FIG. 10.

Among the genes coding for the constant region of feline immunoglobulin κ chain of the present invention, one of the preferable examples is the gene fragment coding for the amino acid sequence as shown in FIG. 12. Such amino acid sequence or nucleotide sequence coding therefor has hitherto never been reported.

One example of the nucleotide sequence of the gene coding for the C region of feline immunoglobulin κ chain of the present invention is as shown in FIG. 11. cDNA coding for the C region of immunoglobulin κ chain can be cloned from a cDNA library of feline antibody-producing cells using the feline immunoglobulin κ chain of the present invention as a probe.

γ Chain of immunoglobulin has also already been found in human and mouse [e.g. A. Shimizu et al., Cell, 29, p121 (1982); N. Takahashi et al., Cell, 29, p671 (1982)] and also reported for other animal species such as rabbit [C. L. Martens et al., Proc. Natl. Acad. Sci. USA, 79, p6018 (1982)] and bovine [K. L. Knight et al., J. Immunol, 140, p3654 (1988)]. However, there has never been any report concerning the feline immunoglobulin γ chain.

The present inventors have obtained a chromosomal gene fragment which will code for the constant region of feline immunoglobulin γ chain by the aforementioned procedure. The present inventors have also cloned cDNA gene coding for the C region of immunoglobulin γ chain from a CDNA library of feline antibody-producing cells using the above chromosomal gene fragment. The cloned gene fragment has genetically been analyzed by comparing an amino acid sequence deduced from the nucleotide sequence of this gene fragment with those of the genes derived from other animal species coding for the C region of immunoglobulin, and as a result, it has been found that the gene fragment obtained by the present invention is a gene fragment coding for the constant region of immunoglobulin γ chain.

The obtained DNA fragment coding for the constant region of feline immunoglobulin γ chain has been analyzed for its nucleotide sequence and an amino acid of the constant region has been determined therefrom. The amino acid sequence has been compared with previously reported amino acid sequences of the constant region of immunoglobulin γ chain derived from human, mouse, rabbit, etc. As a result, it has been found that the amino acid sequence specific for the constant region of feline immunoglobulin γ chain includes the following amino acid sequence (B) in the vicinity of the first cysteine residue counted from the N-terminus of CH1 domain of the constant region of the γ chain:

-Ser-Cys-Gly-Thr-     (B)

The present inventors have found that an amino acid sequence of the above region -Ser-Cys-Gly-Thr- present in the vicinity of the above-mentioned cysteine varies with animal species such as cat, mouse, human, etc. by comparing the amino acid sequence of the constant region of feline immunoglobulin γ chain analyzed by the present invention with the previously analyzed amino acid sequences of the constant region of immunoglobulin γ chain derived from various animals. The present inventors have also found that this region is quite well preserved among subclasses, for example, as an amino acid sequence of the constant region of human γ chain. The above sequence (B) is supposed to be specific for the constant region of feline immunoglobulin γ chain.

Similar sequences specific for the constant region of feline immunoglobulin γ chain have also been found in the vicinity of cysteine at the C-terminal region of the CH1 domain [the following sequence (C)]; at the N-terminal region of the glycosilated site (Asn) of the CH2 domain [the following sequence (D)]; and in the vicinity of cystein at the N-terminal region of CH3 domain [the following sequence (E)]:

-Arg-Trp-Leu-Ser-Asp-Thr-Phe-Thr-Cys-           (C)

-Lys-Thr-Ser-Pro-XXX-XXX-xxx-XXx-XXX-Asn        (D)

-Asn-Lys-XXX-XXX-XXX-XXX-Cys-                   (E)

wherein XXX represents an optional amino acid.

The amino acid sequences of these regions cloned by the present invention have the following sequences (C'), (D') and (E') which are each one of the preferable examples of specific amino acid sequences present in the constant region of feline immunoglobulin γ chain.

-Arg-Trp-Leu-Ser-Asp-Thr-Phe-Thr-Cys-           (C')=(C)

-Lys-Thr-Ser-Pro-Arg-Glu-Glu-Gln-Phe-Asn        (D')

-Asn-Lys-Val-Ser-Val-Thr-Cys-                   (E')

The gene fragment coding for the constant region of the feline immunoglobulin γ chain of the present invention is characterized by that it contains a DNA sequence coding for the above amino acid sequence (B), (C), (D) or (E). These amino acid sequences contained in the γ chain, which are quite important for determining the C region of the feline immunoglobulin γ chain, have been found by the present inventors for the first time.

A preferable example of the constant region of the feline immunoglobulin γ chain containing these amino acid sequences has an amino acid sequence as shown in FIG. 18. Such amino acid sequence and a nucleotide sequence coding therefor have never been reported until the present invention.

An example of the nucleotide sequence of the gene coding for the C region of the feline immunoglobulin γ chain of the present invention includes the sequence as shown in FIG. 17.

On the analogy of the human and mouse cases [for example, A. Shimizu et al., Cell, 29, p121 (1982); N. Takahashi et al., Cell, 29, p671 (1982)], the feline γ chain is also expected to have several subclasses. It is known that there are at least two subclasses of feline γ chain [J. M. Kehoe et al., J. Immunol., 109, p511 (1972)], the gene of the present invention appears to code for one of these two subclasses. In fact, Southern hybridization using the γ gene of the present invention and a feline chromosomal DNA showed an existence of several genes coding for the C regions of other subclasses of the feline γ chain in addition to the γ chain of the present invention. That is, there are genes coding for different subclasses having extremely similar sequences to that of the gene of the present invention. It is believed that the feline γ chain gene of the present invention has sequences which cover also such gene fragments coding for amino acid sequences of different subclasses. Therefore, such gene fragments coding for amino acid sequences of different subclasses can also be used as feline γ chain gene as far as they have substantially the same sequence as that of the gene of the present invention. Such genes coding for C regions of different subclasses can be cloned by using a part of the nucleotide sequence of the present invention as a probe.

As far as the constant region of immunoglobulin is concerned, it is also reported that a genetic analysis of immunoglobulins derived from human, rabbit, etc. showed an existence of an allotype which differs in one to several amino acids within the same class or subclass. Based on the analogy of this fact, it is expected that there exists an allotype for the gene fragment coding for the constant region of the immunoglobulin γ chain of the present invention. Therefore, the gene coding for the constant region of the feline immunoglobuin λ chain, κ chain or γ chain of the present invention is not limited to the gene fragments coding for the above-mentioned amino acid sequences but includes those genes coding for the constant region of different allotypes which have almost the same sequence as the above sequences though containing a partial substitution of an amino acid.

The thus prepared gene coding for the constant region of feline immunoglobulin of the present invention allows for preparation of the feline chimeric antibody using the conventional process for preparing the chimeric antibody [for example, Watanabe et al., Cancer Research, 47, p999–1005 (1987); Japanese Patent First Publication No. 20255/1988]. That is, the chimeric gene can basically be constructed by linking two kinds of gene fragments, i.e. the V region gene and the C region gene, to each other. Since the gene can be classified into mainly two categories depending on a way of isolation, the chimeric antibody can be constructed by using either a combination of V and C region genes isolated from a chromosomal DNA or a combination of V and C region genes isolated from cDNA. The chimeric antibody can be expressed in any expression system such as an animal cell expression system, an E. coli expression system, an yeast expression system, etc. using different expression vectors.

In a combination of the V region and the constant region for preparing the chimeric antibody, a preferable combination is the VH region with the constant region derived from feline H chain such as γ chain, the Vκ region with the constant region of feline κ chain, and the Vλ region with the constant region of feline λ chain, but another combination can also be used. There can be used any V region including those derived from mouse, cat, or other animals, and CDR graft V region [M. Verhoeyen, C. Milstein, G. Winter, Science, 239, p1539 (1987)], as far as it is effective for treating feline diseases (e.g. viral feline diseases, etc.). Thus, although it is described as to the mouse-cat chimeric antibody against feline parvovirus to exemplify the feline chimeric antibody of the present invention, the V region is not limited to that used therein.

The gene fragment coding for feline immunoglobulin provided by the present invention discloses the specific amino acid sequence or DNA sequence in the constant region of feline immunoglobulin, and hence, allows for isolating those genes coding for the constant regions belonging to different subclasses or allotypes. By using the gene coding for the constant region of feline immunoglobulin of the present invention, the feline chimeric antibody can firstly be prepared. The feline chimeric antibody prepared according to the present invention can be used as agents for diagnosis, prevention and treatment of feline diseases which have hitherto never been developed.

The present invention is illustrated by the following Examples in more detail but should not be construed to be limited thereto.

Example 1

Preparation of feline monoclonal antibody-producing cells:

(1) Immunization and preparation of feline lymphocytes:

In order to efficiently obtain activated feline B cells, a complete Freund's adjuvant (CFA: manufactured by Difco)(5 ml) was injected in cats subcutaneously and intraperitoneally for several times at an interval of 2 to 3 weeks for non-specific immunization. Two to three weeks after the final immunization, spleen and lymph node were taken out and a suspension of feline lymphocytes was obtained by crashing with a pincette and pipetting. One cat gave 1 to $5 \times 10^9$ cells from spleen and 1 to $5 \times 10^8$ cells from lymphonode. These lymphocytes were suspended in a complete medium of RPMI 1640 plus 10% fetal calf serum (manufactured by Flow Laboratories) supplemented with L-glutamine (manufactured by Flow Laboratories) at a concentration of 5 to 10×10⁵ cells/ml and thereto was added poke-weed mitogen (PWM: manufactured by Gibco)(2.5 μg/ml), followed by culturing the cells in the presence of 5% $CO_2$ at 37° C. for 2 to 5 days for activation.

(2) Preparation of-mouse myeloma cells:

The myeloma cells employed in the present invention are those derived from mouse Balb/c as described in Köller et al., Nature, 256, p459 (1975) and Eur. J. Immunol., 6, p292 (1976), especially substrains X63-Ag8-6.5.3 and P3-X-63-Ag8-U1, SP2/)0Agl2. These cells were cultured and grown in a complete medium of RPMI 1640 plus 10% fetal calf serum supplemented with glutamine. They were collected just before cell fusion, washed twice with RPMI 1640 medium and resuspended in the same medium for use in cell fusion.

(3) Cell fusion of the feline lymphocytes and the mouse myeloma cells:

The above feline lymphocytes and the mouse myeloma cells were mixed at a ratio of 10:1 or 5:1 (feline lymphocytes:myeloma cells; feline lymphocytes=1×10⁸ cells) and centrifuged at 1,500 rpm for 5 minutes. To the obtained cell pellet was added a 45% polyethylene glycol solution diluted with RPMI 1640 (manufactured by Sigma, pH 7.6, MW 3650; or manufactured by Celba, pH 7.6, MW 4,000)(1 ml) at room temperature over 1 minute. After the mixture was allowed to stand at 37° C. for 5 to 10 minutes, the cells were resuspended by adding RPMI 1640 (40 ml) to the mixture over 6 minutes to quench the cell fusion. The cells were then centrifuged at 1,000 rpm for 10 minutes, the supernatant was removed by suction and the resulting cell pellet was resuspended in RPMI 1640+10% fetal calf serum+HAT (H: hypoxanthine 13.0 μg/ml, A: aminopterin 0.18 μg/ml, T: thymidine 3.87 μg/ml; all manufactured by Sigma) supplemented with glutamine at a concentration of 2 to 10×10⁵ lymphocytes/ml. The suspension was poured into each well of a 96-well microtiter plate at 200 μl/well and was cultured in the presence of 5% $CO_2$ at 37° C. After 5 to 7 days, 50% of the medium was exchanged with the same fresh medium and thereafter the medium exchange was repeated for 5 to 6 times after 10 to 28 days from the cell fusion. By this procedure, only hybridomas were grown, and thereafter the culture was continued until screening assay.

(4) Screening assay and cloning of hybridomas:

Screening assay was conducted to detect a clone which produced a feline IgG antibody using enzyme immunoassay (EIA). A 96-well plate was coated with a goat anti-feline IgG antibody (manufactured by Cappel) and treated with bovine serum albumin (manufactured by Sigma) to block non-specific adsorption and to each well was added the culture supernatant (50 μl) from each well of the hybridoma culture plate. After incubating the plate at 37° C. for 1 to 2 hours, washing was carried out with PBS-T [0.01% Tween manufactured by Katayama Kagaku K.K., 0.01M phosphate buffer, pH 7.2, 0.15M NaCl] four times, a peroxidase-labelled goat anti-feline IgG antibody (manufactured by Cappel, 10,000 fold dilution)(50 μl) was added to each well and plate was incubated at 37° C. for 1 hour. After washing with PBS-T five times, a TMBZ substrate solution (TMBZ: manufactured by Dojin Kagaku K.K., 0.4 mg/ml, hydrogen peroxide: manufactured by Mitsubishi Gasu Kagaku K.K., 0.006%)(50 μl) to develop color. After 10 to 15 minutes, 0.3N $H_2SO_4$ (manufactured by Katayama Kagaku K.K.)(50 μl) was added to each well to quench the reaction and each color development was quantitated with a spectrophotometer (wavelength: 450 nm). The hybridomas in the thus selected feline IgG-producing well were then monoclonalized (cloned) by a limiting dilution procedure. After growth of the clones in each well of the 96-well plate, the above enzyme immunoassay (EIA) was repeated to detect the feline IgG-producing clone. This cloning procedure was repeated at least 3 times to give the cat-mouse hybridoma clone which stably produces feline IgG. This hybridoma clone was successively subjected to an extensive-culture and was kept in the freezed state with a cell-freezing medium of RPMI 1640+HAT+10% DMSO (manufactured by Wako Pure Chemical Industries) supplemented with glutamine in liquid nitrogen.

(5) Characterization of the established hybridoma clone and feline IgG monoclonal antibody produced therefrom:

Measurement with an EIA procedure of an amount of the produced feline antibody confirmed that the established cat-mouse hybridomas were capable of stably producing the feline IgG monoclonal antibody in an amount of 1.0 to 3.0 μg/ml for a long time of 1 year or more and any abnormality was not observed in their ability of producing the antibody.

Figure 1A:
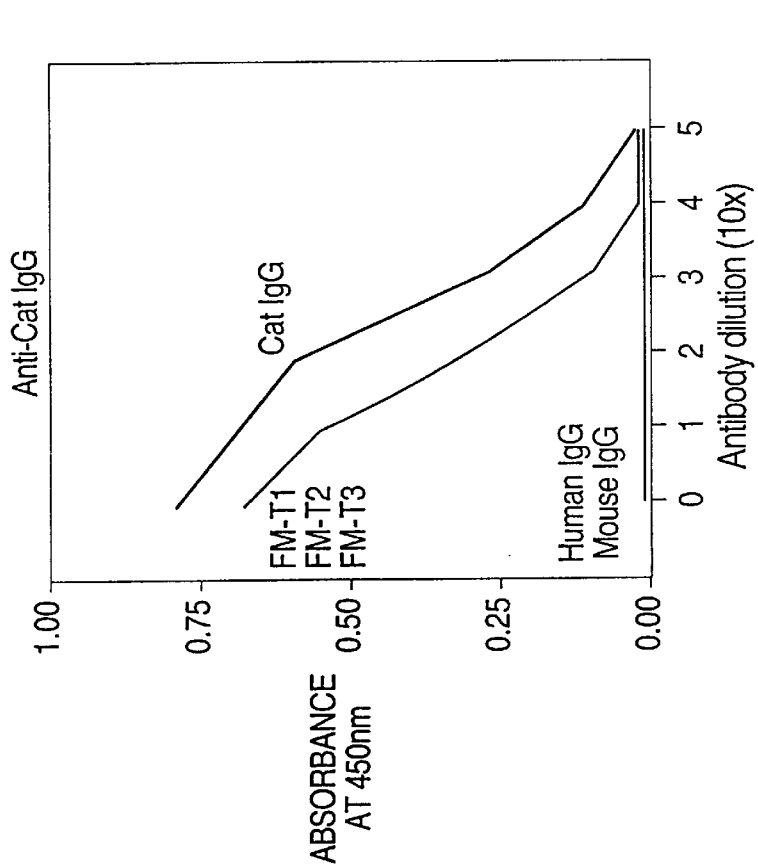
Figure 1C:
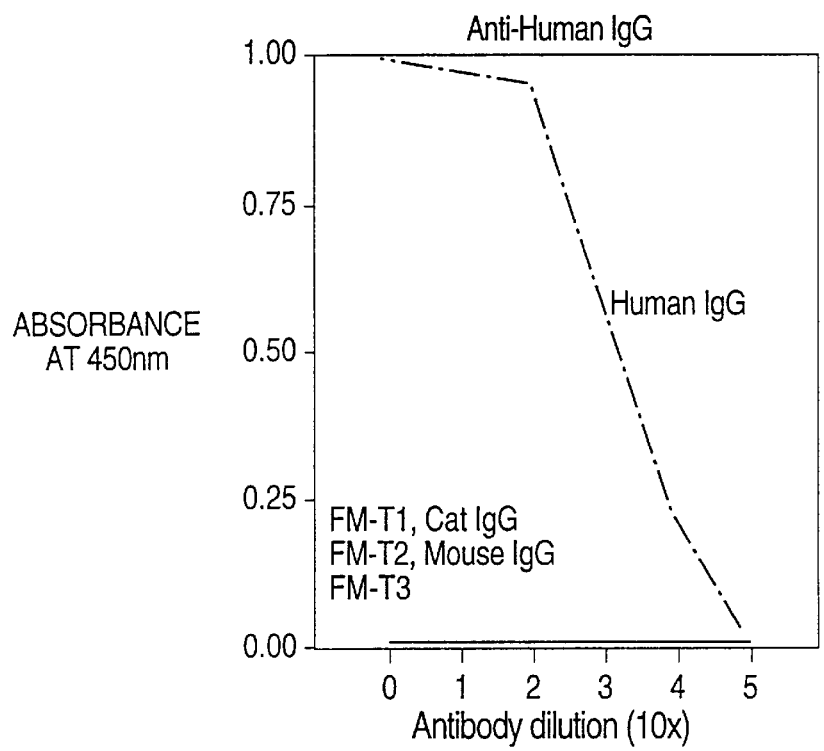
Figure 2:
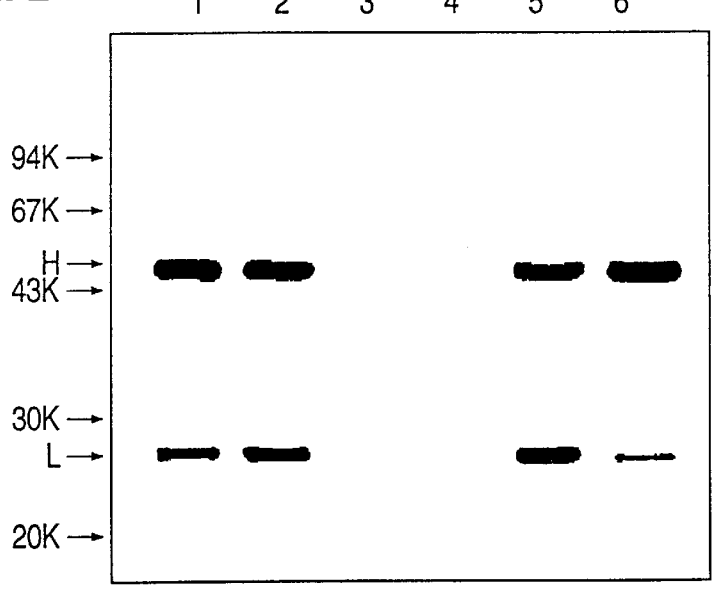
FIG. 2 shows the results of Western blot analysis using an anti-feline antibody proving that IgG produced by the cat-mouse hybridomas prepared by the present invention is a feline monoclonal antibody.

The feline monoclonal antibody produced by the established cat-mouse hybridoma was proved to be feline IgG by an immunoprecipitation method [cf. "Men-eki Jikken Sosaho (Immunological Experimentation)" ed. Jap. Soc. Immunol.]. This antibody was found to be feline IgG antibody since it did not form precipitates with goat anti-mouse IgG serum and goat anti-human IgG serum but did form precipitates with goat anti-feline IgG serum. EIA further proved that the monoclonal antibody was feline IgG antibody since it specifically reacted with only the anti-feline IgG antibody but reacted with neither the anti-human IgG antibody nor the anti-mouse IgG antibody (FIG. 1). Furthermore, Western blotting assay [cf. "Men-eki Jikken Sosaho (Immunological Experimentation)" ed. J. Soc. Immunol.] proved that both the heavy chain (H chain) fragment and light chain (L chain) fragment of the monoclonal antibody specifically reacted only with the anti-feline IgG antibody but did not react with the anti-human IgG antibody or the anti-mouse IgG antibody and that the H chain fragment and the L chain fragment of the monoclonal antibody were identical to those fragments of standard feline IgG antibody in view of molecular weight, showing that the monoclonal antibody is a complete feline IgG monoclonal antibody having both H chain and L chain fragments of the feline IgG antibody (FIG. 2).

In addition, cytoplasmic synthesis of feline IgG antibody was studied by cytoplasmic fluorescent antibody dying assay [cf. "Men-eki Jikken Sosaho (Immunological Experimentation)" ed. Jap. Soc. Immunol.] of the hybridoma clones. As a result, each clone was intracytoplasmically dyed specifically only with the anti-feline IgG antibody but was not dyed with the anti-human IgG antibody and the anti-mouse IgG antibody, proving that the hybridoma clones intracytoplasmically synthesized a complete feline IgG monoclonal antibody.

The cat-mouse heterohybridoma FM-T1 cells producing such feline monoclonal antibody has been deposited under accession number BP-2974 as mentioned hereinbefore. The FM-T1 cells were used in the following Experiment to isolate the constant region of feline immunoglobulin.

Example 2

Cloning of the gene coding for the constant region of feline immunoglobulin λ chain:

(1) Construction of a cDNA library:

Total RNA was separated from the heterohybridoma FM-T1 cells using a guanidium thiocyanate method [J. M.

Ghingwin et al., Biochemistry, 18, p5294 (1979)] and further purified into poly A+RNA using an oligo dT column (Pharmacia). cDNA of the FM-T1 cells was synthesized from the purified poly A+RNA using a cDNA synthesis system Plus (Amersham). EcoRI sites of the synthesized cDNA were methylated with EcoRI methylase (manufactured by Takara Shuzo Co. Ltd.,; the reagents used hereinafter are manufactured by Takara Shuzo Co. Ltd., or Toyobo Co. Ltd., unless otherwise mentioned) and then EcoRI linker was added to the cDNA with T4DNA ligase. This cDNA was completely digested with a restriction enzyme EcoRI and a cDNA having an addition of EcoRI linker was purified with a Bio Gel A50m column (Bio-Rad). The obtained cDNA was ligated to an EcoRI arm of λgt11 vector DNA (Stratagene) with T4DNA ligase and then an in vitro packaging was carried out using kits manufactured by Stratagene to give a cDNA library of the FM-T1 cells.

Figure 3:
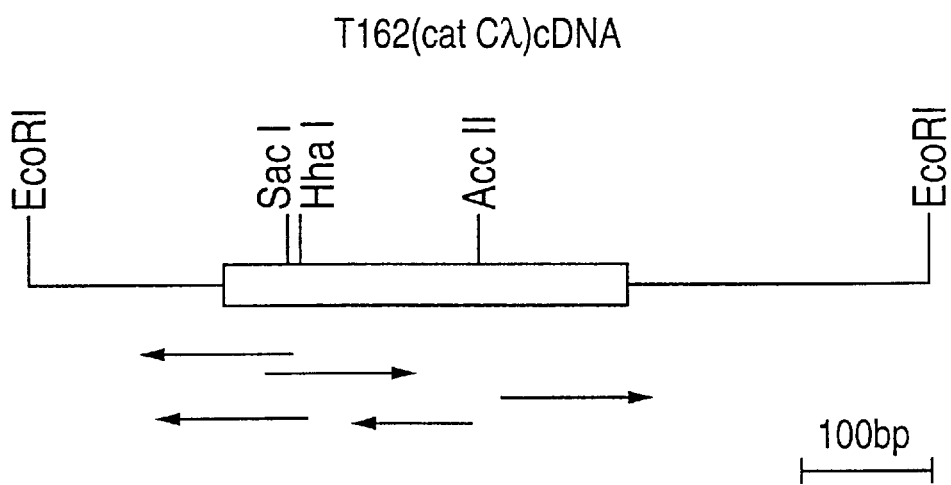
FIG. 3 shows a restriction enzyme map of a DNA fragment (T1-62) coding for the constant region of feline immunoglobulin λ chain cloned by the present invention and the regions (→) in which a nucleotide sequence was analyzed.

(2) Screening of the feline immunoglobulin gene with anti-feline IgG antibody:

Using the cDNA library of FM-T1 cells constructed as mentioned above, *E. coli* Y1090 strain cells infected with the phage λgt11 were poured onto an LB plate [laboratory dish of No.2 square manufactured by Eiken Kizai charged with 1.5% Bacto-agar manufactured by Gifco, 1% Bacto-tryptone manufactured by Gifco, 0.5% Bacto-yeast extract manufactured by Gifco, 0.25% NaCl manufactured by Wako Pure Chemical Industries, pH 7.5] so that 50,000 plaques per plate of the λgt11 phage were formed and cultured at 42° C. for 3 hours. After covering a nitrocellulose filter (NC filter: Code BA85 manufactured by S&S) soaked with 10 mM IPTG (manufactured by Wako Pure Chemical Industries) on the plate, the culture was continued at 37° C. for additional 4 hours. The NC filter was peeled off the plate, washed with a W buffer [WB: 7 mM Tris buffer, pH 7.2, 150 mM NaCl, 0.005% Tween 20] and immersed in a BLOTTO [5% skim milk, 10 µl/100 ml Antifoam A] at 4° C. overnight. Then the BLOTTO was exchanged with a BLOTTO containing an anti-feline IgG antibody [manufactured by Cappel; 10 µg/ml; treated with a 1% *E. coli* lysate (manufactured by Bio-Rad) at 4° C. overnight] and the reaction was conducted at room temperature for 2 hours. After washing the NC filter with WB five times, the NC filter was immersed in an incubation buffer [PBS, pH 7.2, 0.005% Tween 20, 1% BSA] containing a peroxidase-labelled goat IgG antibody [manufactured by Cappel; treated with a 1% *E. coli* lysate (manufactured by Bio-Rad) at 4° C. overnight] and the reaction was conducted at room temperature for 2 hours. After washing the NC filter with WB five times, the NC filter was immersed in a color development solution containing 5% HRP color develoment reagent (manufactured by Bio-Rad) and 0.5% $H_2O_2$ (manufactured by Wako Pure Chemical Industries) to proceed color development. After selection of the phage corresponding to the plaque which showed the color development on the NC filter, the phage was further cloned. The clone was selected in this way which reacted with the anti-feline IgG antibody and finally a clone T1-62 was obtained. This clone had a 0.7 kb size and seemed to be a gene coding for the immunoglobulin λ chain in accordance with the nucleotide sequence analysis as described hereinafter. FIG. 3 shows a restriction enzyme map of this clone. The EcoRI insertion fragment of this clone was isolated from the phage DNA in accordance with a method by Thomas and Davis [M. Thomas and R. W. Davis, J. Mol. Biol., 91, p315 (1974)] and subcloned into the EcoRI site of pUC18 vector.

Figure 4:
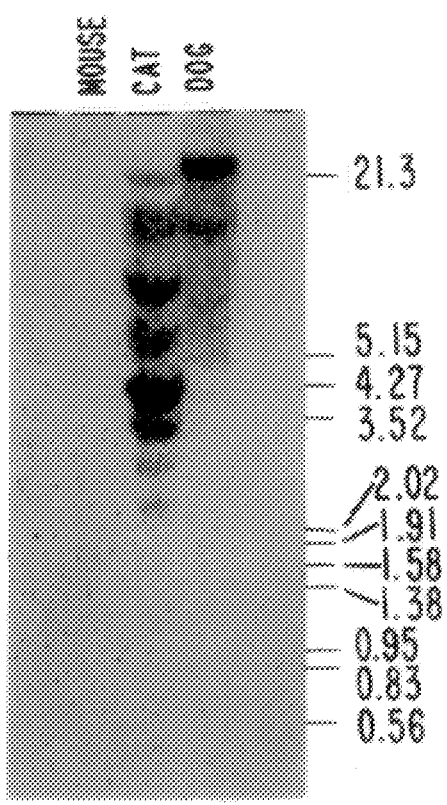
FIG. 4 shows the results of Southern hybridization analysis where a DNA fragment (T1-62) coding for the constant region of feline immunoglobulin λ chain cloned by the present invention is hybridized with a chromosomal DNA (EcoRI digestion) of feline hepatocyte.

(3) Southern blotting and Northern blotting analysis using T1-62:

Southern blotting analysis was carried out using T1-62. A chromosomal DNA (10 µg) from feline, canine and mouse hepatocytes was digested with the restriction enzyme EcoRI and the obtained DNA fragments were subjected to electrophoresis using 0.7% agarose gel. After transfer to a nylon membrane filter (Gene Screen Plus, NEN Research Product), the southern hybridization was carried out with a [$^{32}$P]-labelled T1-62 probe containing the constant region of the feline λ chain. The southern hybridization was carried out in accordance with a protocol of a manual attached to the Gene Screen Plus. The molecular size was calculated based on a marker DNA which was prepared by digesting the λ phage DNA with HindIII. As shown in FIG. 4, several bands having various sizes from about 2 to about 20 kb were detected. This suggests that the gene coding for the C region of feline λ chain has more than one subclass, which can also be estimated on the analogy of the cases of human and mouse [P. A. Hieter et al., Nature, 294, p536 (1981); G. F. Hollis et al., Nature, 296, p321 (1982); B. Blomberg et al., Proc. Natl. Acad. Sci. USA, 79, p53 (1982); J. Miller et al., Nature, 295, p428 (1982)]. Since it is known that the gene coding for the C λ region is amplified in wild mice [C. L. Scott et al., Nature, 300, p757 (1982)], the gene coding for the C region of the feline λ chain can also presumably be subjected to amplification.

Figure 5:
FIG. 5 shows the results of Northern hybridization analysis where a DNA fragment (T1-62) coding for the constant region of feline immunoglobulin λ chain cloned by the present invention is hybridized with poly A+RNA of FM-T1 cells (lane 1) or poly A+RNA of FM-T2 cells (lane 2)

Northern blotting was then conducted. The RNA for use in the hybridization was prepared by separating a whole RNA from FM-T1 and FM-T2 cells using a guanidium thiocyanate method [J. M. Ghingwin et al., Biochemistry, 18, p5294 (1979)] and purifying the whole RNA into a poly A+RNA with oligo dT column (Pharmacia). The RNA (2 µg) was electrophoresed using 0.75% agarose gel containing 3% formaldehyde. After transfer to a nylon membrane filter (Gene Screen Plus), a northern hybridization was carried out with a [$^{32}$P]-labelled T1-62 probe. The northern hybridization was carried out in accordance with a protocol of a manual attached to the Gene Screen Plus. As a result, this probe detected a band at about 1.3 kb in both mRNAs (FIG. 5). This size is almost the same as that of the gene coding for immunoglobulin λ chain known in mouse and human.

From the above two results, the T1-62 gene was presumed to be an active gene coding for a functional feline Cλ region.

(4) Nucleotide sequence and amino acid sequence of T1-62:

In order to determine a nucleotide sequence of T1-62, small DNA fragments EcoRI-SacI, SacI-AccII, AccII-EcoRI and EcoRI-HhaI were prepared (FIG. 3) from T1-62. These small fragments were blunt-ended with T4-DNA polymerase and inserted into a SmaI site of a M13mp19 vector using a Takara Ligation Kit. Competent cells of JM101 were prepared in accordance with a Toyobo Instructions Manual and transformed with M13mp19 DNA wherein the Cλ gene was inserted, followed by extraction and purification of a single stranded DNA. A nucleotide sequence of this single stranded DNA was determined using a Takara M13 Sequencing Kit and Fuji Gencer Gel System. The direction of determination of the nucleotide sequence is shown in FIG. 3. As a result of the determination of the nucleotide sequence, it was confirmed that the feline λ chain gene consisted of V, J and C regions. FIG. 6 shows the results thereof. An amino acid sequence deduced from this nucleotide sequence suggested that the gene is in an open reading frame and is not a pseudogene (FIG. 7).

A homology of the nucleotide sequence of T1-62 was searched on data bases, LASL and EMBL, using a software of genetic analysis (Genetyx Ver.6 manufactured by Software Kaihatsu, K.K.). As a result, the highest homology was shown with that of human immunoglobulin λ chain gene but no homology was shown with that of genes other than the immunoglobulin λ chain gene. Homological comparison of the Cλ region of the T1-62 gene with those of mouse and human showed 75.8% homology with mouse and 81.3% homology with human in the nucleic acid level and 69.5% homology with mouse and 77.1% homology with human in the amino acid level.

As is clear from the above results, the T1-62 gene is surely a gene coding for the feline λ chain which can be used for the preparation of a feline chimeric antibody.

Example 3

Cloning of the gene coding for constant region of feline κ chain:

(1) Conditions of crosshybridization:

The L chain of feline immunoglobulin is known to be mainly consisted of λ chain [L. Hood et al., Cold Spring Harbor Symp. Quant. Biol. 32, p133–146 (1967)], and hence, it is foreseeable that only quite a few lymphocytes express κ chain. In fact, the cat-mouse heterohybridomas as described above were λ chain-producing cells. Therefore, the present inventors have considered that it would be very difficult to obtain the desired gene from messenger RNAs of polyclonal antibody-producing cells by a cDNA cloning procedure, and hence, have tried to isolate the desired gene fragment coding for the constant region of feline immunoglobulin κ chain from a chromosomal DNA of feline hepatocyte under crosshybridization conditions using the constant region of human κ chain (human Cκ) as a probe.

For cloning of the feline κ chain gene by a crosshybridization procedure, conditions of crosshybridization with human κ chaim were studied. The gene coding for the human Cκ region used for the crosshybridization was a gene cloned from a human culture cell ARH77 strain [ATCC CRL 1621] which is available from professor Takeshi Watanabe, Department of Molecular Immunology, Medical Institute of Bioregulation, Kyushu University [cf. Kudo et al., Gene, 33, p181 (1985); Nishimura et al., Cancer Res., 47, p999 (1987)]. From this human Cκ gene, an EcoRI-EcoRI fragment containing Cκ exon was obtained and used as a probe.

Figure 8:
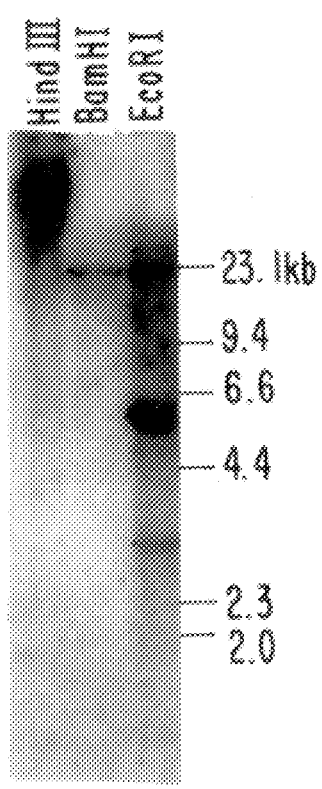
FIG. 8 shows the results of Southern hybridization analysis where an EcoRI fragment of a chromosomal DNA of feline hepatocyte is hybridized with a [$^{32}$P]-labelled probe containing human Cκ chain region.

Chromosomal DNAs were isolated from feline hepatocytes according to N. Blin and D. W. Stafford [Nuc. Acids. Res., 3, p2303 (1976)] and each 10 μg each of the chromosomal DNA was digested with the restriction enzyme EcoRI. DNA fragments obtained by the restriction enzyme digestion were subjected to electrophoresis using 0.7% agarose gel. The developed DNAs were transferred to a nitrocellulose membrane filter (BA85 manufactured by S&S) and then southern hybridization was carried out with a [$^{32}$P]-labelled DNA probe containing human Cκ region gene. The southern hybridization was carried out in a solution of 6×SSC [0.09M $Na_3C_6H_5O_7·2H_2O$, 0.9M NaCl], 10 mM EDTA [manufactured by Dojin Kagaku] and 0.5% SDS [manufactured by Bio-Rad] at 65° C. overnight. The final washing of the filter was conducted with a solution of 0.1×SSC and 0.1% SDS at 45° C. for 15 minutes. Autoradiography of this filter showed a band at about 5.5 kb as shown in FIG. 8. The molecular size was calculated from a marker DNA prepared by digesting λ phage DNA with HindIII. This DNA fragment of 5.5 kb appears to contain the gene coding for feline κ chain and was used for cloning.

(2) Isolation of the gene coding for feline κ chain:

A chromosomal DNA (100 μg) from feline hepatocytes was completely digested with EcoRI and DNA fragments of 5.5 kb were prepared by a sucrose density gradient centrifugation [sucrose 10 to 40% (wt/vol), 26,000 rpm, 18 hours, 15° C.]. The obtained DNA fragments were then ligated to an EcoRI arm of λ gt11 vector DNA (manufactured by Stratagene) with T4 DNA ligase and an in vitro packaging was carried out using a kit available from Stratagene to give a κ chain gene library of feline hepatocytes. Plaque hybridization [W. D. Benton, R. W. Davis, Science, 196, p180 (1977)] was conducted using a human Cκ probe under the same conditions as those of the above crosshybridization and a clone CEκ8a containing a feline Cκ chain exon was selected from the library. FIG. 10 shows a restriction enzyme map of this clone. The EcoRI insertion fragment of this clone was isolated from the phage DNA in accordance with a method by Thomas and Davis [M. Thomas and R. W. Davis, J. Mol. Biol., 91, p315 (1974)] and subcloned into the EcoRI site of pUC18 vector.

(3) Southern blotting and Northern blotting analysis using CEκ8a:

A chromosomal DNA (10 μg) from feline hepatocytes was digested with the restriction enzyme EcoRI and the Southern blotting analysis was conducted using the clone CEκ8a in the same manner as described in Example 2 (3). A pattern of the detected bands was compared with that from crosshybridization using a human Cκ chain probe previously conducted, and as a result, a band was observed at the same position (about 5.5 kb). This result presumably showed that the feline Cκ region gene consists of a single gene without any other subtypes. This is also suggested by the cases of human and mouse [P. A. Hieter et al., Cell, 22, p197 (1989); E. E. Max et al., Proc. Natl. Acad. Sci. USA, 76, p3450 (1979)].

Figure 9:
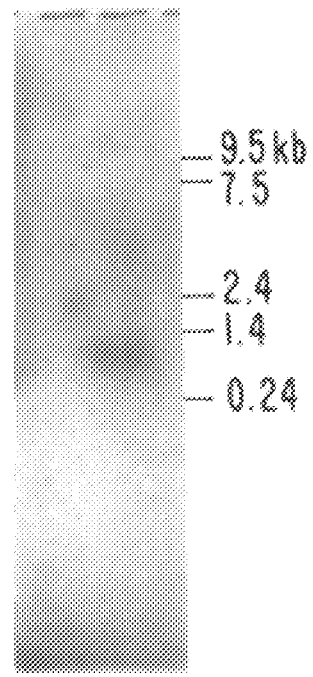
FIG. 9 shows the results of Northern hybridization analysis where poly A+RNA extracted from feline spleen cells is hybridized with a [$^{32}$P]-labelled CEκ8a probe.

Northern blotting analysis was then carried out using the CEκ8a clone in the same manner as described in Example 2 (3). As a result, the probe detected a band at about 1.3 kb with mRNA from feline spleen cells (FIG. 9). This is almost the same size as known in the mouse and human immunoglobulin κ chain gene.

These two results presumably showed that the CEκ8a is an active gene containing a gene coding for a functional feline Cκ region.

(4) Nucleic acid and amino acid sequences of the CEκ8a:

In order to determine a nucleic acid sequence of the gene coding for the feline Cκ region, a DNA fragment (XbaI-AvaI fragment) of about 2.0 kb containing the Cκ region was isolated from the clone CEκ8a and recloned into a XbaI-AvaI site of pUC18 vector. This plasmid was prepared in a large amount in accordance with the conventional method [for example, T. Maniatis "Molecular Cloning" Cold Spring Harbor Lab. (1982)] and from the XbaI-AvaI fragments were prepared small DNA fragments (XbaI-DdeI, DdeI-HaeIII, HaeIII-HinfI, XbaI-RsaI). These small DNA fragments were blunt-ended with T4-DNA polymerase and then inserted into a SmaI site of M13mpl9 vector using a Takara Ligation Kit. The nucleotide sequence was determined in the same manner as described in Example 2 (4). A direction of determination of the nucleotide sequence is shown in FIG. 10. As a result of the determination of the nucleic acid base sequence, the Cκ gene comprising a single exon was confirmed. FIG. 11 shows the results thereof. An amino acid sequence deduced from the nucleotide sequence showed that the gene is in an open reading frame and is not a pseudogene (FIG. 12).

A homology of the nucleotide sequence of CEκ8a2 was searched on data bases, LASL and EMBL, using a software of genetic analysis (Genetyx manufactured by Software Kaihatsu, K.K.). As a result, a high homology was shown with genes coding for human and mouse immunoglobulins κ chain but no homology was shown with genes other than the immunoglobulin κ chain gene. Homological comparison of the Cκ region of the CEκ8a gene with the mouse and human Cκ regions showed 73.3% homology with mouse and 73.0% homology with human in the nucleic acid level and 54.7% homology with mouse and 59.6% homology with human in the amino acid level.

As is clear from the above results, the CEκ8a gene is surely a gene coding for the feline κ chain which can be used for the preparation of the cat-mouse chimeric antibody.

Example 4

Cloning of the gene coding for constant region of feline γ chain:

(1) Conditions of crosshybridization:

The present inventors then tried to isolate the feline γ chain gene by cloning using a crosshybridization procedure as in the case of κ chain gene.

Figure 13:
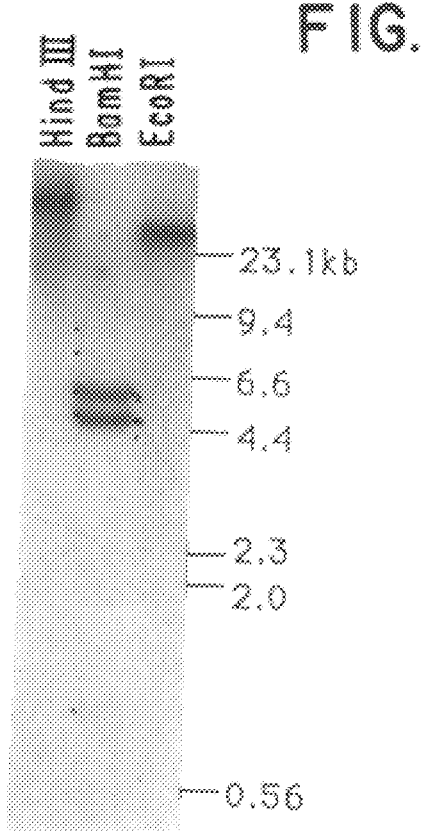
FIG. 13 shows the results of Southern hybridization analysis where a BamHI fragment of a chromosomal DNA of feline hepatocyte is hybridized with a [$^{32}$P]-labelled probe containing the human Cγl chain region.

In the same manner as in Example 3 (1), crosshybridization was carried out using a chromosomal DNA (10 μg) from feline hepatocytes digested with the restriction enzyme BamHI and a human Cγ1 chain as a probe. The gene coding for the human Cγ1 region used for the crosshybridization was a gene cloned from a human culture cell ARH77 strain [ATCC CRL 1621] which is available from professor Takeshi Watanabe, Department of Molecular Immunology, Medical Institute of Bioregulation, Kyushu University [Kudo et al., Gene, 33, p181 (1985); Nishimura et al., Cancer Res., 47, p999 (1987)]. Computerized analysis of homology between mouse, human and rabbit γ chains showed an extremely high homology especially at the region containing a CH2–CH3 exon. Therefore, a PstI-SphI fragment containing the CH2–CH3 exon was obtained from the human Cγ1 gene and used as a probe. The result of autoradiography showed two bands at about 5.8 kb and 5.5 kb as shown in FIG. 13. These bands were targetted for cloning.

Figure 14:
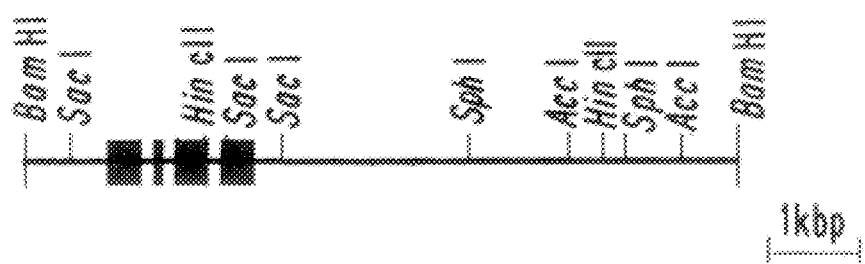
FIG. 14 shows a restriction enzyme map of the chromosomal DNA fragment (CB25γ7c) coding for the constant region of feline immunoglobulin γ chain cloned by the present invention.

(2) Isolation of the feline γ chain gene:

A chromosomal DNA (100 μg) from feline hepatocytes was completely digested with BamHI and then DNA fragments corresponding to the above 5.5 kb and 5.8 kb were prepared by a sucrose density gradient centrifugation [sucrose 10 to 40% (wt/vol), 26,000 rpm, 18 hours, 15° C.]. Then, the obtained DNA fragments were ligated to a BamHI-digested DNA of Charomid 9-42 vector DNA (manufactured by Nippon Gene) with T4 DNA ligase and an in vitro packaging was carried out using a kit available from Stratagene. LE392 *E. coli* (Stratagene) was then infected with the resultant vector DNA and a γ chain gene library of feline hepatocytes was obtained. Colony hybridization [up-to-date: Idenshisosa Jikken Jitsuyo Handbook (Handbook for Practice of Gene Manipulation) p426] was conducted under the same conditions as those of the above described crosshybridization and a clone CB25γ7c containing the feline Cγ chain exon was selected from the library using the human Cγ1 probe. This clone had a size of about 5.8 kb and was one of two bands shown in the above Southern blotting analysis. FIG. 14 shows a restriction enzyme map thereof. This plasmid clone was prepared in a large amount in accordance with the conventional method [for example, T. Maniatis "Molecular Cloning" Cold Spring Harbor Lab. (1982)] and a BamHI insertion fragment was isolated. For easier handling, the fragment was cleaved with SacI and a DNA fragment (SacI fragment) of about 1.3 kb assumed to contain the Cγ exon were isolated and recloned into a SacI site of pUC18 vector.

(3) Southern and Northern blotting analysis using CB25γ7c:

A chromosomal DNA (10 μg) from feline hepatocytes was digested with the restriction enzyme BamHI and Southern blotting analysis was conducted using the CB25γ7c clone in the same manner as described in Example 2 (3). Comparison of a pattern of detected bands with that of crosshybridization previously conducted using the human Cγ1 chain probe showed a band at the same position (about 5.8 kb and 5.5 kb)(the same results as in FIG. 13). This result showed an existence of several Cγ region genes of different subclasses belonging to the same feline γ chain in addition to the CB25γ7c.

The existence of several subclasses in the feline γ chain is also suggested on the analogy of the cases of human and mouse [for example, A. Shimizu et al., Cell, 29, p121 (1982); N. Takahashi et al., Cell, 29, p671 (1982)]. It is known that serologically at least two subclasses exist for the feline γ chain [J. M. Kehoe, J. Immunol., 109, p511 (1972)] and the CB25γ7c gene seems to code for either of the two subclasses.

Figure 15:
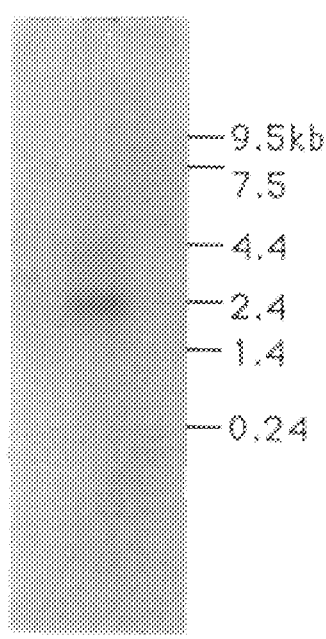
FIG. 15 shows the result of Northern hybridization analysis where poly A+RNA extracted from feline antibody-producing heterohybridoma FM-T1 is hybridized with a [$^{32}$p]-labelled CB25γ7c probe.

Then, Northern blotting analysis was carried out using the CB25γ7c clone in the same manner as described in Example 2 (3). As a result, the probe detected a band at about 1.8 kb with mRNAs from cat-mouse heterohybridoma FM-T1cells (FIG. 15). This has almost the same size as known in mouse and human immunoglobulin γ chain genes.

These two results presumably showed that the CB25γ7c clone is an active gene containing a gene coding for a functional feline Cγ region.

Figure 16:
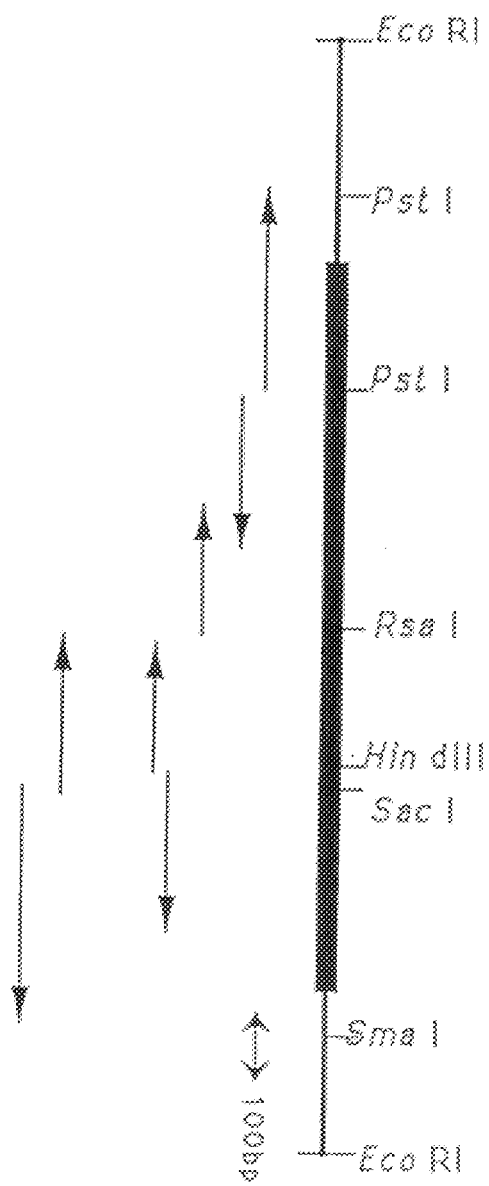
FIG. 16 shows a restriction enzyme map of a cDNA fragment T1CB1a cloned by the present invention and the regions (→) in which a nucleotide sequence was analyzed.

(4) Isolation of feline γ chain cDNA clone:

It is presumed that the feline Cγ region has an exon-intron structure on the analogy of the mouse and human cases. In order to determine a nucleotide sequence of the exon part of the feline Cγ region, it is necessary to clone a CDNA from mRNA of feline immunoglobulin γ chain where splicing has been completed. As mentioned above, the cat-mouse heterohybridoma FM-T1 cells synthesized a mRNA hybridizable with the CB25γ7c clone. Therefore, the present inventors tried to clone a cDNA of feline γ chain from a cDNA library of FM-T1 cells using the CB25γ7c as a probe. The construction of the cDNA library of FM-T1 cells has already been described in Example 2 (1). From this library, a clone T1CB1a containing cDNA coding for feline immunoglobulin Cγ chain is selected by a plaque hybridization procedure [W. D. Benton, R. W. Davis, Science, 196, p180 (1977)] using the CB25γ7c as a probe. This clone has a 1.5 kb size and a restriction enzyme map thereof is shown in FIG. 16. An EcoRI insertion fragment of this clone was isolated from the phage DNA in accordance with Thomas and Davis [W. Thomas, R. W. Davis, J. Mol. Biol., 91, p315 (1974)] and recloned at the EcoRI site of pUC18.

(5) Nucleotide sequence and amino acid sequence of T1CB1a:

In order to determine a nucleotide sequence of the gene coding for feline Cγ region, small DNA fragments (PstI-PstI, PstI-RsaI, PstI-HindIII, SacI-SmaI, EcoRI-SacI, HindIII-EcoRI) were prepared. These small fragments were blunt-ended using T4 DNA polymerase and then inserted at the SmaI site of M13mpl9 vector using a Takara Ligation Kit. The nucleotide sequence was determined in the same manner as described in Example 2 (4). A direction to determine the nucleotide sequence is shown in FIG. 16. As a result of the determination of the nucleotide sequnece, it was confirmed that the feline γ gene comprised V, D, J and C. FIG. 17 shows the results thereof. An amino acid sequence was then deduced from the nucleotide sequence, and as a result, it was shown that the gene was in an open reading frame and was not a pseudogene (FIG. 18).

Homology of the nucleotide sequence of T1CB1a was searched on data bases, LASL and EMBL, using a software for genetic analysis (Genetyx manufactured by Software Kaihatsu K.K.). As a result, a high homology was shown with genes coding for human and mouse immunoglobulin γ chains but no homology was shown with genes other than immunoglobulin γ chain gene. Homological comparison of the Cγ region of T1CB gene with the mouse and human Cγ region genes showed 70.2% homology with mouse γ1 and 76.8% homology with human G1 in the nucleotide sequence level and 61.0% homology with mouse γ1 and 69.7% homology with human G1 in the amino acid sequence level.

The above results confirmed that the CB25γ7c and T1CB1a genes were surely genes coding for feline γ chain which can be used for a mouse-cat chimeric antibody.

Example 5

Preparation of mouse-cat chimeric antibody:

(1) Isolation of gene coding for mouse immunoglobulin κ chain variable (VK) region:

In order to show usefulness of the thus isolated gene coding for the constant region of feline immunoglobulin in the preparation of the chimeric antibody, a chimeric antibody comprising said gene and a gene coding for the variable region of mouse antibody JP2 having a neutralization activity against canine parvovirus (CPV) was prepared. It is known that a monoclonal antibody capable of neutralizing canine parvovirus can also neutralize feline parvovirus because of the high homology between the canine and feline parvoviruses.

Figure 19:
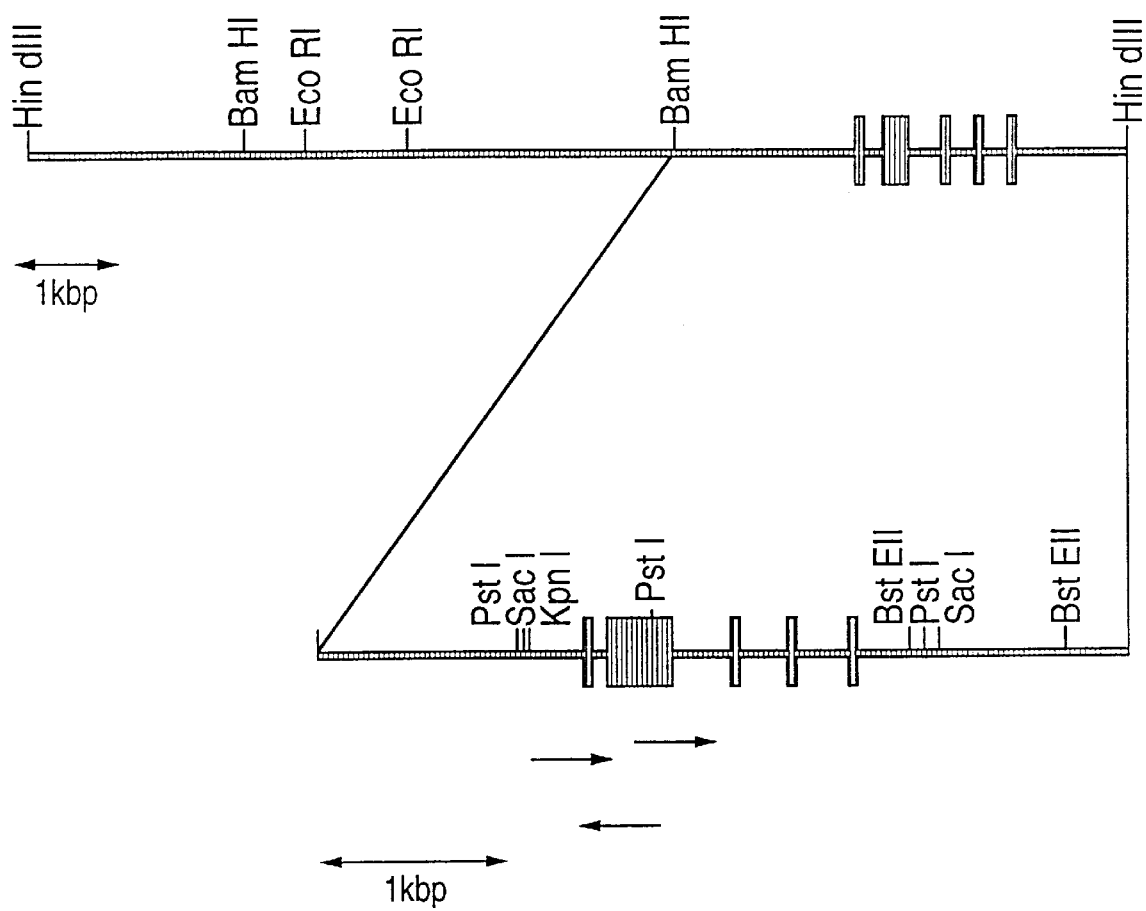
FIG. 19 shows a restriction enzyme map of a clone JP2gL411 containing Vκ region gene isolated from anti-CPV mouse monoclonal antibody-producing cells.

The gene coding for the Vκ region of JP2 antibody was firstly isolated. A chromosomal DNA (100 µg) isolated from hybridomas JP2(γl,κ) producing an anti-CPV antibody was digested with the restriction enzyme HindIII. This DNA fragment was then ligated to λL47 vector DNA (Amersham) with T4 DNA ligase and a chromosomal DNA library of JP2 cells was obtained. A clone JP2gL411 containing the Vκ region gene of the anti-CPV antibody was selected from the library by a plaque hybridization procedure [W. D. Benton, R. W. Davis, Science, 196, p180 (1977)] using a mouse Jκ probe [E. E. Max et al., J. Biol. Chem., 256, p5116 (1981)]. FIG. 19 shows a restriction enzyme map thereof. From this gene fragment there was prepared a BamHI-HindIII fragment containing a Vκ exon part and the fragment was subjected to Northern hybridization with mRNAs of JP2 and its mother strain P3x63Ag8.U1 to detect a JP2 specific band at 1.3 Kbp. A nucleotide sequence was determined (FIG. 20) by a DNA sequencing which was made at a direction of an arrow as shown in FIG. 19. An amino acid sequence deduced from the nucleotide sequence was in an open reading frame, and hence, the gene was shown to code for a functional immunoglobulin Vκ. Based on these results, this Vκ gene was used for praparing a gene coding for an L chain of a mouse-cat chimeric antibody.

Figure 21:
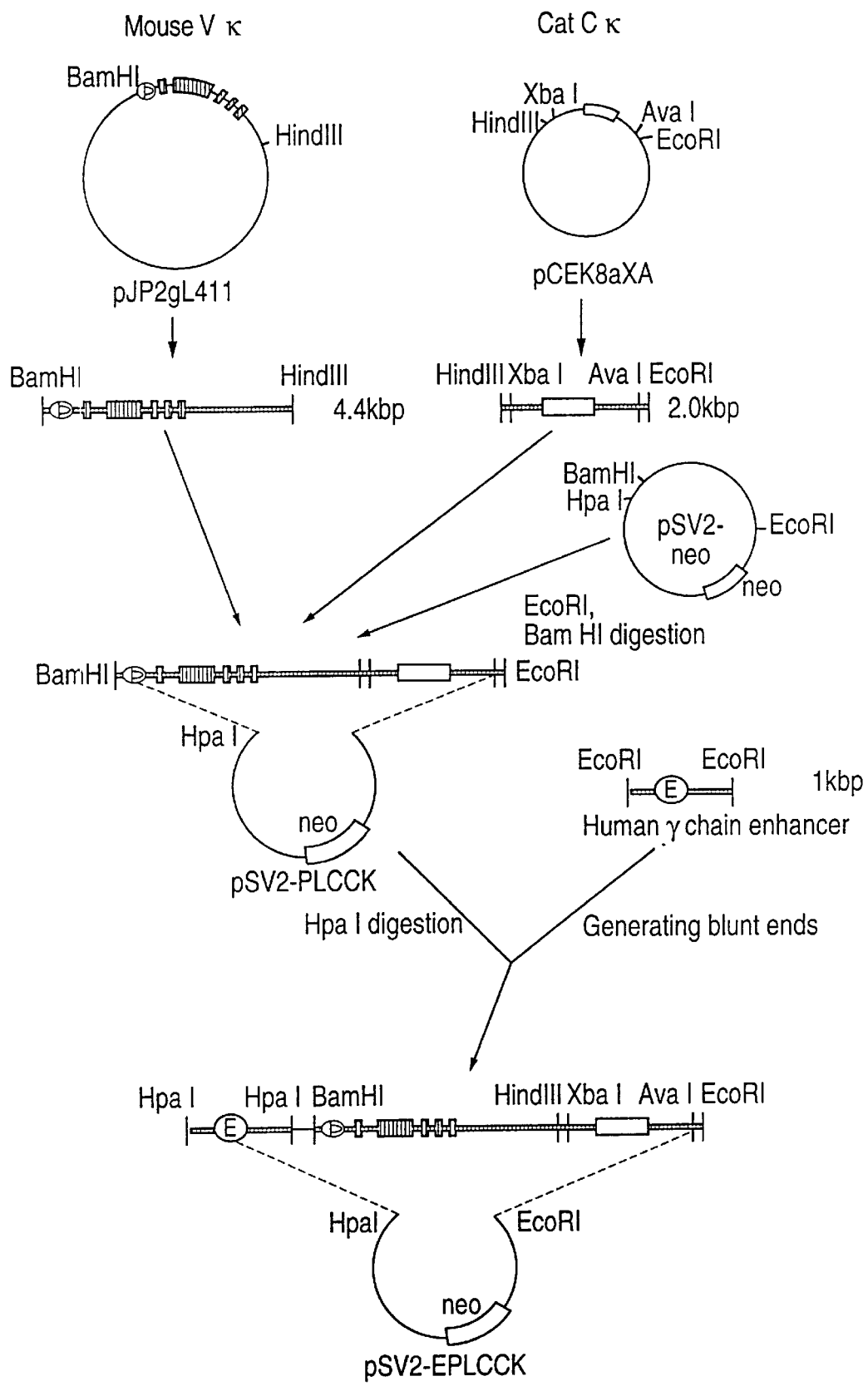
FIG. 21 shows a construction of a gene (pSV2-EPLCCκ) expressing an L chain of an anti-CPV mouse-cat chimeric antibody.

(3) Preparation of gene coding for L chain of mouse-cat chimeric antibody (pSV2-EPLCCκ):

The plasmid pCEκ8aXA prepared in Example 3 (2) was digested with HindIII and EcoRI to prepare a HindIII-EcoRI DNA fragment of 2 kb containing a gene coding for feline immunoglobulin Cκ chain. On the other hand, a plasmid pJP2gL411 containing the gene coding for mouse immunoglobulin Vκ chain prepared in Example 5 (1) was digested with BamHI and HindIII to prepare a gene of 4.4 kb coding for a mouse immunoglobulin Vκ-Jκ region. These genes were ligated to each other together with pSV2-neo vector [P. J. Southern et al., J. Mol. Appl. Genet., 1, p327 (1982)] which was digested with EcoRI and BamHI using a Takara Ligation Kit to prepare a plasmid pSV2-PLCCκ. The human heavy chain enhancer element was inserted into the HpaI site of this plasmid to prepare a plasmid pSV2-EPLCCκ (FIG. 21).

(5) Expression of mouse-cat chimeric antibody:

The constructed plasmid pSV2-EPLCCκ was introduced into a mouse B lymphocyte strain Sp2/0-Ag12 (ATCC CRL 1581) in accordance with a method previously reported by Maeda et al. [Japanese Patent First Publication No. 20255/1988] using a DEAE-dextran method. The cells were tranformed with the plasmid pSV2-EPLCCκ to prepare cells which produce the desired L chain of the mouse-cat chimeric antibody.

As mentioned above, only use of the gene coding for the constant region of feline immunoglobulin as cloned by the present inventors makes it possible to prepare the feline chimeric antibody. The thus prepared feline chimeric antibody can be used as agents for diagnosis, prevention and treatment of feline disease, especially feline infectious diseases.

What is claimed is:

1. A gene fragment which comprises a DNA sequence encoding an amino acid sequence of a constant region of cat-mouse heterohybridoma feline immunoglobulin L chain, wherein said immunoglobulin L chain is a feline immunoglobulin λ chain or κ chain.

2. The gene fragment according to claim 1 wherein said amino acid sequence of said constant region is such that amino acid residues 7 and 8, at the N-terminal region of the first cysteine counted from the N-terminal of a polypeptide of the constant region of said λ chain are serine and alanine respectively.

3. The gene fragment according to claim 2 wherein the amino acid sequence at the N-terminal region of the first cysteine counted from the N-terminus of a polypeptide of the constant region of said λ chain is as follows:

-Ser-Ala-Asn-Lys-Ala-Thr-Leu-Val-Cys-.

4. The gene fragment according to claim 3 wherein the amino acid sequence of a constant region includes the following amino acid sequence of from 11th to 9th amino acids at the N-terminal region of the second cysteine at the C-terminus of a polypeptide of the constant region of said λ chain:

-Pro-Asn-Glu-.

5. The gene fragment according to claim 1 wherein the constant region comprises a polypeptide having the following amino acid sequence:

—Gln—Pro—Lys—Ser—Ala—Pro—Ser—Val—Thr—Leu—Phe

—Pro—Pro—Ser—Ser—Glu—Glu—Leu—Ser—Ala—Asn—Lys

—Ala—Thr—Leu—Val—Cys—Leu—Val—Ser—Asp—Phe—Tyr

—Pro—Ser—Gly—Leu—Thr—Val—Ala—Trp—Lys—Glu—Asp

—Gly—Thr—Pro—Ile—Thr—Lys—Gly—Val—Glu—Thr—Thr

—Lys—Pro—Ser—Arg—Gln—Ser—Asn—Asn—Lys—Tyr—Ala

—Ala—Ser—Ser—Tyr—Leu—Ser—Leu—Ser—Pro—Asn—Glu

—Trp—Lys—Ser—His—Ser—Arg—Tyr—Thr—Cys—Gln—Val

—Thr—His—Glu—Gly—Ser—Thr—Val—Glu—Lys—Ser—Val

—Val—Pro—Ala—Glu—Cys—Pro.

6. The gene fragment according to claim 3 which contains the following DNA sequence:

AGC GCA AAC AAG GCC ACC CTG GTG TGT.

7. The gene fragment according to claim 5 which contains the following DNA sequence:

CAG CCC AAG TCG GCC CCC TCG GTC ACA CTC TTC

CCA CCC TCC AGT GAG GAG CTC AGC GCA AAC AAG

GCC ACC CTG GTG TGT CTC GTC AGT GAC TTC TAC

CCC AGC GGC TTG ACG GTG GCC TGG AAG GAA GAT

GGC ACC CCC ATC ACC AAG GGC GTG GAG ACC ACC

AAG CCC TCC AGA CAG AGC AAC AAC AAG TAC GCG

GCC AGC AGC TAC CTG AGC CTG TCA CCG AAC GAG

TGG AAA TCT CAC AGC AGA TAC ACC TGC CAG GTC

ACG CAC GAG GGG AGC ACT GTG GAG AAG AGT GTG

GTC CCT GCA GAG TGC CCT TAG.

8. The gene fragment according to claim 1 wherein said constant region comprises a polypeptide having 109 amino acids and the amino acid sequence of four amino acids at the C-terminus is -Cys-Gln-Arg-Glu-.

9. The gene fragment according to claim 1 wherein the polypeptide of the constant region has the following amino acid sequence:

Ser Asp Ala Gln Pro Ser Val Phe Leu Phe Gln

Pro Ser Leu Asp Glu Leu His Thr Gly Ser Ala

Ser Ile Val Cys Ile Leu Asn Asp Phe Tyr Pro

Lys Glu Val Asn Val Lys Trp Lys Val Asp Gly

Val Val Gln Thr Lys Ala Ser Lys Glu Ser Thr

Thr Glu Gln Asn Ser Lys Asp Ser Thr Tyr Ser

Leu Ser Ser Thr Leu Thr Met Ser Arg Thr Glu

Tyr Gln Ser His Glu Lys Phe Ser Cys Glu Val

Thr His Lys Ser Leu Ala Ser Thr Leu Val Lys

Ser Phe Asn Arg Ser Glu Cys Gln Arg Glu.

10. The gene fragment according to claim 9 which has the following DNA sequence:

AGT GAT GCT CAG CCA TCT GTC TTT CTC TTC CAA

CCA TCT CTG GAC GAG TTA CAT ACA GGA AGT GCC

TCT ATC GTG TGC ATA TTG AAT GAC TTC TAC CCC

AAA GAG GTC AAT GTC AAG TGG AAA GTG GAT GGC

GTA GTC CAA ACA AAG GCA TCC AAG GAG AGC ACC

ACA GAG CAG AAC AGC AAG GAC AGC ACC TAC AGC

CTC AGC AGC ACC CTG ACG ATG TCC AGG ACG GAG

TAC CAA AGT CAT GAA AAG TTC TCC TGC GAG GTC

ACT CAC AAG AGC CTG GCC TCC ACC CTC GTC AAG

AGC TTC AAC AGG AGC GAG TGT CAG AGA GAG TAG.

11. A recombinant DNA molecule coding for an amino acid sequence of an L chain of a mouse-cat chimeric antibody which comprises a gene fragment coding for an amino acid sequence of a variable region of a mouse immunoglobulin L chain and a gene fragment coding for an amino acid sequence of a constant region of a feline immunoglobulin L chain wherein the latter gene fragment is linked to the 3' site of the former gene fragment.

12. The recombinant DNA molecule according to claim 11 wherein the gene fragment coding for the amino acid sequence of the constant region of the feline immunoglobulin L chain is a gene fragment coding for the amino acid sequence of the constant region of a feline immunoglobulin κ chain.

13. The recombinant DNA molecule according to claim 12 wherein said constant region has a poly-peptide comprising 109 amino acids and the amino acid sequence of four amino acids at the C-terminus is -Cys-Gln-Arg-Glu-.

14. The recombinant DNA molecule according to claim 13 wherein the constant region of the feline immunoglobulin κ chain has the following amino acid sequence:

Ser Asp Ala Gln Pro Ser Val Phe Leu Phe Gln

Pro Ser Leu Asp Glu Leu His Thr Gly Ser Ala

Ser Ile Val Cys Ile Leu Asn Asp Phe Tyr Pro

Lys Glu Val Asn Val Lys Trp Lys Val Asp Gly

Val Val Gln Thr Lys Ala Ser Lys Glu Ser Thr

-continued

Thr Glu Gln Asn Ser Lys Asp Ser Thr Tyr Ser

Leu Ser Ser Thr Leu Thr Met Ser Arg Thr Glu

Tyr Gln Ser His Glu Lys Phe Ser Cys Glu Val

Thr His Lys Ser Leu Ala Ser Thr Leu Val Lys

Ser Phe Asn Arg Ser Glu Cys Gln Arg Glu.

15. The recombinant DNA molecule according to claim 14 wherein the gene fragment coding for the amino acid sequence of the constant region of the feline immunoglobulin κ chain has the following DNA sequence:

AGT GAT GCT CAG CCA TCT GTC TTT CTC TTC CAA

CCA TCT CTG GAC GAG TTA CAT ACA GGA AGT GCC

TCT ATC GTG TGC ATA TTG AAT GAC TTC TAC CCC

AAA GAG GTC AAT GTC AAG TGG AAA GTG GAT GGC

GTA GTC CAA ACA AAG GCA TCC AAG GAG AGC ACC

ACA GAG CAG AAC AGC AAG GAC AGC ACC TAC AGC

CTC AGC AGC ACC CTG ACG ATG TCC AGG ACG GAG

TAC CAA AGT CAT GAA AAG TTC TCC TGC GAG GTC

ACT CAC AAG AGC CTG GCC TCC ACC CTC GTC AAG

AGC TTC AAC AGG AGC GAG TGT CAG AGA GAG TAG.

16. The recombinant DNA molecule according to claim 11 wherein the gene fragment coding for the amino acid sequence of the variable region codes for an amino acid sequence which is specifically reactive with feline parvovirus.

17. The recombinant DNA molecule according to claim 16 wherein the gene fragment coding for the amino acid sequence of the variable region has the following DNA sequnece:

GAC ATC CAG ATG AAC CAG TCT CCA TCC AGT CTG

TCT GCA TCC CTT GGA GAC ACA ATT ACC

ATC ACT TGC CAT GCC AGT CAG AAC ATT AAT GTT

TGG TTA AGC TGG TAC CAG CAG AAA CCA GGA AAT

ATT CCT AAA CTA TTG ATC TAT AAG GCT TCC AAA

TTG CAC ACA GGC GTC CCA TCA AGG TTT AGT GGC

-continued

AGT GGA TCT GGA ACA GGT TTC ACA TTA ACC ATC

AGC AGC CTG CAG CCT GAA GAC ATT GCC ACT TAC

TAC TGT CAA CAC GGT CAA AGT TAT CCG TAC AGC

TTC GGA GGG GGG ACC AAG CTG GAA ATA AAA CGT

AAG TAG TCT TCT CAA.

18. A polypeptide of a mouse-cat chimeric antibody L chain which is expressed from a cell transformed with an expression vector for cells wherein a recombinant DNA molecule coding for an amino acid sequence of the mouse-cat chimeric antibody L chain is incorporated, said recombinant DNA molecule comprising a gene fragment coding for an amino acid sequence of a variable region of a mouse immunoglobulin L chain and a gene fragment coding for an amino acid sequence of a constant region of a feline immunoglobulin L chain in which the latter gene fragment is linked to the 3' site of the former gene fragment.

19. The polypeptide according to claim 18 wherein the constant region of the chimeric antibody L chain is a feline immunoglobulin 78 chain.

20. The polypeptide according to claim 19 wherein said constant region has a polypeptide comprising 109 amino acids and the amino acid sequence of four amino acids at the C-terminus is -Cys-Gln-Arg-Glu.

21. The polypeptide according to claim 19 wherein said constant region has the following amino acid sequence:

Ser Asp Ala Gln Pro Ser Val Phe Leu Phe Gln

Pro Ser Leu Asp Glu Leu His Thr Gly Ser Ala

Ser Ile Val Cys Ile Leu Asn Asp Phe Tyr Pro

Lys Glu Val Asn Val Lys Trp Lys Val Asp Gly

Val Val Gln Thr Lys Ala Ser Lys Glu Ser Thr

Thr Glu Gln Asn Ser Lys Asp Ser Thr Tyr Ser

Leu Ser Ser Thr Leu Thr Met Ser Arg Thr Glu

Tyr Gln Ser His Glu Lys Phe Ser Cys Glu Val

Thr His Lys Ser Leu Ala Ser Thr Leu Val Lys

Ser Phe Asn Arg Ser Glu Cys Gln Arg Glu.

22. The polypeptide according to claim 18 wherein the variable region of the antibody has an amino acid sequence which is specifically reactive with feline parvovirus.

23. The polypeptide according to claim 22 wherein the variable region has the following amino acid sequence:

| | | | | | | | | | |
|---|---|---|---|---|---|---|---|---|---|
| Asp | Ile | Gln | Met | Asn | Gln | Ser | Pro | Ser | Ser | Leu |
| Ser | Ala | Ser | Leu | Gly | Asp | Thr | Ile | Thr | Ile | Thr |
| Cys | His | Ala | Ser | Gln | Asn | Ile | Asn | Val | Trp | Leu |
| Ser | Trp | Tyr | Gln | Gln | Lys | Pro | Gly | Asn | Ile | Pro |
| Lys | Leu | Leu | Ile | Tyr | Lys | Ala | Ser | Lys | Leu | His |
| Thr | Gly | Val | Pro | Ser | Arg | Phe | Ser | Gly | Ser | Gly |
| Ser | Gly | Thr | Gly | Phe | Thr | Leu | Thr | Ile | Ser | Ser |
| Leu | Gln | Pro | Glu | Asp | Ile | Ala | Thr | Tyr | Tyr | Cys |
| Gln | His | Gly | Gln | Ser | Tyr | Pro | Tyr | Ser | Phe | Gly |
| Gly | Gly | Thr | Lys | Leu | Glu | Ile | Lys. | | | |

24. The gene fragment according to claim 1 wherein the feline immunoglobulin L chain is the feline immunoglobulin λ chain.

25. The gene fragment according to claim 1 wherein the feline immunoglobulin L chain is the feline immunoglobulin κ chain.

26. A gene fragment according to claim 1, wherein said amino acid sequence is such that amino acid residues 7, 8, and 15 at the N-terminal region of the first cysteine counted from the N-terminus of a polypeptide of the constant region of said λ chain are serine, alanine and cysteine, respectively.

27. A cat-mouse heterohybridoma which produces feline immunoglobulin.

28. The heterohybridoma according to claim 27 wherein an L-chain of said feline immunoglobulin belongs to the λ class.

29. The heterohybridoma according to claim 28, wherein the amino acid sequence of a constant region of said L-chain is such that amino acid residues 7 and 8 at the N-terminal region of the first cysteine counted from the N-terminus of a polypeptide of the constant region of said λ chain are serine, alanine and cysteine, respectively.

30. The hybridoma according to claim 29 wherein the amino acid sequence at the N-terminal region of said cysteine is as follows:

-Ser-Ala-Asn-Lys-Ala-Thr-Leu-Val-Cys-.

31. The hybridoma according to claim 28 wherein the L chain includes the following amino acid sequence of from 11th to 9th amino acids at the N-terminal region of the second cysteine counted from the C-terminus of the polypeptide of the constant region of said λ chain:

-Pro-Asn-Glu-.

32. The hybridoma according to claim 28 wherein the L chain includes the following amino acid sequence of the polypeptide of the constant region of said λ chain:

—Gln—Pro—Lys—Ser—Ala—Pro—Ser—Val—Thr—Leu—Phe
—Pro—Pro—Ser—Ser—Glu—Glu—Leu—Ser—Ala—Asn—Lys
—Ala—Thr—Leu—Val—Cys—Leu—Val—Ser—Asp—Phe—Tyr
—Pro—Ser—Gly—Leu—Thr—Val—Ala—Trp—Lys—Glu—Asp
—Gly—Thr—Pro—Ile—Thr—Lys—Gly—Val—Glu—Thr—Thr
—Lys—Pro—Ser—Arg—Gln—Ser—Asn—Asn—Lys—Tyr—Ala
—Ala—Ser—Ser—Tyr—Leu—Ser—Leu—Ser—Pro—Asn—Glu
—Trp—Lys—Ser—His—Ser—Arg—Tyr—Thr—Cys—Gln—Val
—Thr—His—Glu—Gly—Ser—Thr—Val—Glu—Lys—Ser—Val
—Val—Pro—Ala—Glu—Cys—Pro.

33. A process for preparing a feline immunoglobulin gene which comprises synthesizing cDNAs from poly A+RNAs of cat-mouse heterohybridomas, transforming a host cell with a vector in which each of said cDNAs is incorporated, obtaining expression products in each host cell, and screening a transformant which produces the feline immunoglobulin with an anti-feline immunoglobulin antibody.

* * * * *